US011835448B2

(12) United States Patent
Auad

(10) Patent No.: US 11,835,448 B2
(45) Date of Patent: Dec. 5, 2023

(54) EQUIPMENT AND METHOD FOR ANALYSIS OF A FLUID

(71) Applicant: Rogério Baptista Auad, Porto Alegre (BR)

(72) Inventor: Rogério Baptista Auad, Porto Alegre (BR)

( * ) Notice: Subject to any disclaimer, the term of this patent is extended or adjusted under 35 U.S.C. 154(b) by 277 days.

(21) Appl. No.: 17/292,082

(22) PCT Filed: Sep. 6, 2019

(86) PCT No.: PCT/BR2019/050381
§ 371 (c)(1),
(2) Date: Jun. 7, 2021

(87) PCT Pub. No.: WO2020/093121
PCT Pub. Date: May 14, 2020

(65) Prior Publication Data
US 2021/0396653 A1 Dec. 23, 2021

(30) Foreign Application Priority Data
Nov. 8, 2018 (BR) .......................... 1020180730223

(51) Int. Cl.
*G01N 21/25* (2006.01)
*G01N 21/15* (2006.01)
(Continued)

(52) U.S. Cl.
CPC .......... *G01N 21/251* (2013.01); *G01N 21/15* (2013.01); *G01N 21/25* (2013.01); *G01N 21/255* (2013.01);
(Continued)

(58) Field of Classification Search
CPC .... G01N 21/251; G01N 21/255; G01N 33/32; G01N 2021/0193; G01N 2021/152; G01N 2021/3155
See application file for complete search history.

(56) References Cited

U.S. PATENT DOCUMENTS

| 3,740,156 A | * | 6/1973 | Heigl | ....................... G01N 1/10 250/576 |
| 6,533,449 B1 | * | 3/2003 | Auad | .................... B01F 35/834 366/132 |
| 2008/0273204 A1 | | 11/2008 | Peixoto et al. | |

FOREIGN PATENT DOCUMENTS

| BR | 9612756 A | 10/1999 |
| BR | 9801134 A | 11/2006 |

(Continued)

OTHER PUBLICATIONS

International Search Report and Written Opinion of the International Searching Authority from Application No. PCT/BR2019/050381 dated Dec. 23, 2019.

(Continued)

*Primary Examiner* — Uzma Alam
*Assistant Examiner* — Mohamed Doumbia
(74) *Attorney, Agent, or Firm* — Troutman Pepper Hamilton Sanders LLP; Ryan A. Schneider; Chris N. Davis

(57) ABSTRACT

There is described an equipment and method for analysis of a fluid, suspension, solution, dispersion or fluid emulsion that automatically analyzes the characteristic properties of the samples of the fluids, such as paints, enamels, and dyes, among others, so that adjustments can be made to the fluid to meet the optical properties such as color, opacity, hue, saturation (tinting power), covering and luminosity, from the (Continued)

spectrometric measurement technique by transmission analysis of film having radiated fixed thickness.

15 Claims, 27 Drawing Sheets

(51) Int. Cl.
  *G01N 21/84* (2006.01)
  *G01N 33/32* (2006.01)
  *G01N 21/01* (2006.01)
  *G01N 21/31* (2006.01)
(52) U.S. Cl.
  CPC ............ *G01N 21/84* (2013.01); *G01N 33/32* (2013.01); *G01N 2021/0193* (2013.01); *G01N 2021/152* (2013.01); *G01N 2021/3155* (2013.01)

(56) References Cited

FOREIGN PATENT DOCUMENTS

| | | |
|---|---|---|
| CN | 104166154 A | 11/2014 |
| DE | 19618773 C1 | 11/1997 |
| EP | 0932829 A1 | 8/1999 |
| EP | 2161555 A1 | 3/2010 |
| JP | 2001074661 A | 3/2001 |
| WO | 2005003740 A1 | 1/2005 |
| WO | 2013173401 A1 | 11/2013 |

OTHER PUBLICATIONS

International Preliminary Report on Patentability Chapter I from Application No. PCT/BR2019/050381 dated Dec. 23, 2019.

\* cited by examiner

EQUIPMENT AND METHOD FOR ANALYSIS OF A FLUID

FIELD OF INVENTION

The present application describes an equipment and method for analysis of a fluid, suspension, solution, dispersion, or fluid emulsion. More specifically, it comprises an equipment that automatically analyzes the characteristic properties of samples of fluids, such as paint, enamels, and dyes, among others, so that adjustments can be made to the fluid to reach the optical properties, such as color, opacity, and hue, saturation (tinting power), covering and luminosity, from the spectrometric measurement technique by transmission analysis of film having irradiated fixed thickness, in the range from 50 to 1000 microns.

BACKGROUND OF THE INVENTION

The term paint can be defined as being a liquid, pasty, or solid pigmented composition, which, when applied in a thin layer (film) over an appropriate surface, in the state in which it is provided or after dilution, is convertible, after a certain period, into a solid, colored, translucent, or opaque film.

The main constituents of a paint are: (a) resin, which is usually a translucent or transparent medium, where its main function is to promote the adherence of the paint layer over the substrate, being further responsible for humidifying the pigments, brightness aspects, chemical resistance, physical resistance, among others; (b) pigments and fillers that promote the development of the color, film opacity, resistance to radiations, optical properties, among others; (c) additives that provide to the film physical, chemical, rheological properties, among others; (d) solvents or thinners that are used basically to adjust the characteristics of viscosity and applicability of the paint over the substrate, evaporating at the conclusion of this process and enabling the cure/drying of the formed film.

The pigments, different from the dyes, can be described as solid substances, finely divided and practically insoluble in the vehicle, which are used in the preparation of paints with the purpose of granting them color, opacity, or other special characteristics. That is, they are used with the intention of modifying the optical properties of a paint, as well as the properties of the products that are incorporated therein. One relevant property which characterizes the pigments is the capacity that they hold to allow obtaining the colors that it is desired to imitate, whereby their presence may also be necessary to obtain opacity, since the paints, in their majority, are used to cover the surfaces over which they are applied.

In a process for production of paint, enamel, or pigment bases, the raw materials are mixed in different proportions to produce a fluid with a set of desired physical properties. One inherent problem to this process is associated to the variations of the raw materials that are used and the variability of the manufacturing process itself. These reasons make it unviable that a simple mixture in pre-defined proportions of the constituents reaches, in a direct manner, the required specifications.

Therefore, it is necessary for the desired specifications to be reached, that, during the manufacturing process, several physical properties of this fluid be measured, and several adjustments be made, which ends up representing variations in the constituting proportions of the formula, batch by batch, of the manufactured product Among the several properties of a paint, the optical properties, such as color, brightness and covering power are extremely relevant. In this case, visual or spectrophotometric techniques are currently used for the analysis. In both techniques, the paint is applied in the form of a uniform film over a test substrate to observe the color, opacity, brightness thereof, among others. After drying or curing, the paint is analyzed and compared with a standard. With the use of spectrophotometric technique, the colorimetric and optical characteristics can be measured with precision.

In both types of analyses, due to the procedures related to the preparation, application, cure/drying, among others, the analysis period can take hours or even days, depending on the case.

For the simple analysis of the characteristics related exclusively to the color of a paint, it is essential that the film applied over a substrate has total covering (opacity) since, otherwise, the color of the substrate will directly influence the measurement of the final color observed, both by visual method as spectrophotometric.

To measure the colors in a manner that is equivalent to the observation by the human eye, there are used spectrophotometers that measure the physical properties of the reflected light (% of reflectance) along the visible specter, comprised between 400 to 700 nanometers. In this case, the graphic that is generated, having as abscissa axis the wavelength and as ordinate axis the reflectivity percentage obtained, characterizes in an effective manner the color of the paint film, making it equivalent to a "fingerprint" of that color.

From the commercial point of view, there currently exist two manners of paint commercialization, namely:

Factory Pack, where these paints are produced directly in the factories and delivered already in the final containers, whereby all their properties have already been adjusted during the manufacturing process, such as the color, the covering, the density, the viscosity among others;

Commercial tintometric systems, where the paints, which are commercialized by means of this method are obtained by means of the mixtures of pigment pastes with previously adjusted bases, dosed in "tintometric machines", directly at the points of sale.

In the case of the paints produced by tintometric machines, since there does not exist any subsequent analysis of the quality control for the paint that is commercialized by this method, it becomes vital that all these characteristics, both of the adjusted bases as those of the pigment pastes, are precisely controlled so that they can be dosed precisely and generate a product that is completely within the specifications.

This method presumes that all the components that will be used are perfect in their properties so that the paint that is obtained at the conclusion of the mixture meets all the specifications thereof, such as the color, the covering, the density, the viscosity, among others.

In this manner, both methods for preparation of paints have an extremely large conceptual difference, considering that the product that is obtained by means of the factory pack process admits that the components that comprise the formulation of the product, such as resins, pigment pastes, bases, among others, do not require being previously adjusted, since there will be a subsequent adjustment/quality control step, which step will compensate and adjust the characteristics of the final product, while the paints produced by means of the commercial tintometric systems must mandatorily have the quality parameters of the components strictly controlled, so that the final product, without being tested, meets all the desired properties.

As mentioned, the bases and/or pigment pastes in tintometric systems need to be previously adjusted for their subsequent dosage, considering that the variability of the raw materials that are provided by the manufacturers (pigments/fillers/etc.), further associated to the variations in the vehicles and the manufacturing process itself for these bases, does not allow an acceptable reproducibility that waives the need for analysis and adjustments.

In this case, for the purpose of adjustments, a simple observation of the color in these bases or pigment pastes, whether by visual method or spectrophotometric, does not translate what will happen when these bases are mixed for the preparation of a paint, since they are in a state called "full saturation".

In this state, since these techniques do not have sensitivity to identify differences between samples, the "desaturation" or "cutting" method is adopted, by means of standard dilution with a previously calibrated pigmented base.

The result of this mixture, within the previously determined proportions, allows measuring of a property called "tinting strength" or "dyeing strength" or even simply "strength".

The measuring of the strength, for analysis and adjustment of the colored pigment pastes, is usually carried out using a standardized and calibrated white base, produced with $TiO_2$ (titanium dioxide) pigment. For the analysis and adjustment of white bases, usually standardized and calibrated bases are used, produced from black or green pigments.

In this case, the analysis and adjustment technique of a determined dyeing consists in weighing a pre-defined quantity of a standardized base and another quantity, also pre-defined of pigment paste which it is intended to analyze/adjust. The product that is generated from the mixture of these constituents is applied to a substrate, cured, or dried in pre-established conditions and compared to a physical standard, by visual technique or in a spectrophotometric standard, by means of the reflection curve that is obtained.

In a simplified form in case the color obtained by means of this technique is more intense than that of the standard, this indicates that the pigment paste under analysis must undergo dilution with the original transparent vehicle of this paste, until the expected result is reached. In case it is less intense, this means that a higher concentration of pigments in the mixture must be used to reach the result.

This same technique is valid and used both for colored pigment pastes as for white pastes and bases.

It must be emphasized, however, that this measurement and strength adjustment technique, regardless of the manner of estimating the differences between the standard and the sample (visual or with spectrophotometer), brings by itself an extremely relevant temporal variability connected to the calibration of standards.

As an example, we can imagine that a black standard used to calibrate a white standard, had as origin a previous white standard, which was also calibrated by a previous black standard and so on "ad infinitum". This ends up by introducing a permanent and continued degradation in the colorimetric characteristics of the standards, comparable to making photocopies from photocopies repeatedly, thus occurring a degradation in the characteristics and in the quality of each successive document.

Apart from this problem, additional variabilities are added to this technique, which are related to errors related to the weighing of the paint components; method of preparation of the surface; pressure of the spray used to apply the paint on the surface; thickness of the coating applied; temperature of curing/drying; relative humidity of the air; stability of the bases (flocculation and re-agglomeration); losses due to evaporation with consequent concentration of standards; human factors, among others.

All these factors, jointly, produce an extremely relevant variability for the paint manufacturers, which generates, apart from the operational complexity, several other associated costs, such as: "no quality" costs, high stocks, lead time for analysis and adjustments, loss of operational capacity, among others.

More recently the state of the art describes an equipment that measures the transmission specter of fluids with different refractive indexes by means of a device having automatic control of the thickness of the film, alternative to the conventional desaturation technique.

In this case, the base or pigment paste is contained within two surfaces that are permeable to radiation (optical windows) in the visible specter, illuminated on one side by means of a light source and observed by means of a spectrophotometer on the opposite side.

The equipment allows that the distance (optical path) is varied, within the two optical windows, reducing the thickness of the film until there is obtained a thickness through which the luminous radiation can cross the irradiated film, there being obtained the emergent spectral radiation curve through the opposite optical window.

In this methodology a pure colorimetric vision is obtained from the colorimetric characteristics of the pigment under analysis, while in the conventional desaturation technique something is obtained which represents the effect which the pigment paste generates when mixed to a white pigment, that is, the equivalent to a deformation in the spectral curve of the standard white pigment when the pigment paste under analysis is added, in a determined concentration.

Document BR9612756 describes a system for analysis of fluids, destined to analyze a specific physical characteristic of the fluid, and a method for the same, the said system having a film formation device to form a fluid film with a specified thickness, a film irradiation device adapted to irradiate the film with an electromagnetic radiation to produce an interaction radiation containing information that is associated with the specified physical characteristic of the fluid, a receptor, to receive the interaction radiation, and a detector, associated with the receptor, to detect the interaction radiation. The film formation device comprises a sample region defined between opposite contact surfaces with the fluid, the referred sample region being in communication with a fluid entry to allow feeding the fluid to the same, to form a fluid film having the thickness thereof defined by the distance between the opposite contact surfaces with the fluid, at least one of the opposite contact surfaces with the fluid being permeable to electromagnetic radiation.

Document BRPI9801134 describes an apparatus for continuous preparation of a fluid, such as paints, enamels, and dyes, to produce a resulting fluid having desired pre-defined physical properties, such as color, opacity, hue, saturation, luminosity, density and/or viscosity, with automatic adjustment of the physical characteristics of the fluid; and which is capable of measuring the properties of the concentrates and bases, determining the ingredients and the quantifies thereof that are required to correct any variations in the physical properties required from the concentrate or base, automatically providing the correct quantity of ingredients that are necessary to make the correction, guaranteeing that the final product has products that are within the specific limits for the fluid. The apparatus of the invention is characterized by the fact that, while the referred physical characteristic detected of the fluid is different from the desired referred physical characteristic, the exit means, and the entry means of the mixer mean are interconnected to allow that the referred fluid returns to the referred mixer means.

Document US2008273204 describes an apparatus and method for measuring the spectral properties of a paint, dye, enamel, or other opaque fluid, both in transmission as in reflection, wherein a lock-in amplifier is used to substantially increase the signal-sound relation of the transmission components of the electromagnetic radiation passing through the fluid, thus allowing that the measurements of the transmittance are made in the order of 0.0001% or less of the incident electromagnetic radiation, avoiding, in this manner, the dilution of the sample, which generates uncertainties in the measurement or using very thin film fluids to increase transmittance, which can have as inconvenience the fact that the radiation cannot interact sufficiently with the fluid to provide a spectrum of transmissibles.

Document US20080273204 describes a device and method for measuring the transmission and reflection of a liquid sample, particularly paint or other opaque liquid, comprising a referenced light source, a beam-splitter ("switcher"), a measurement cell gap for adjustable measurement, at least one reception optic and at least one detector and plug-in amplifier. A beam splitter can divide the luminous beam originating from a light source through a fiberglass, whereby it is possible to achieve a simultaneous or separate measurement of the transmission and reflection. By dislocating the position of the beam splitter, the illumination angles and thus the reflection angle, can be adjusted. In the same manner, the second electromagnetic radiation transmitted can be detected in a 45° angle.

Document WO2005003740 describes reflectance sensors comprising an optical unit, a sample analysis unit and a control unit, a method for measuring the reflectance of a sample in the form of a liquid pigment or a solid pigmented surface, and the use of a reflectance sensor to measure the reflectance of the liquid pigment preparations in different procedural stages during the production, additional processing, and application of the referred liquid pigment preparations.

Document WO2013173401 refers to a method for measuring one or more properties of a liquid, comprising the preparation of a thin film of fluid sample having a predetermined film thickness in the range from 0.05 mm to 2 mm; a circular planar disk having a first disk surface and a second disk surface on opposite sides of the planar circular disc, the circular planar disk being coupled to a rotation shaft aligned with rotational axis of the circular planar disk, perpendicular to the disk surface for providing rotation to the circular planar disk; a device frame that positions the circular planar disk and the rotation shaft; a thickness control device comprising a thin film setting edge coupled to a liquid return channel and at least one frame connector and a motion control device coupled to the rotation shaft to allow rotation of the rotation device and a motion control device to control the rotation speed, rotation direction or a combination of the two rotation elements.

Document EP0932829 describes a system for analysis of the properties of paints, pigment pastes, or similar systems, which consist in a device for forming a film of paints, pigment pastes and similar systems having a specific thickness, a light source to irradiate the paint to be examined or constructed pigment paste or similar systems to be examined, wherein there occurs an interaction between light and the paint, the pigment paste or similar systems, wherein a measurement signal is generated; and a device for receiving the measurement signal and a detector connected to the device to receive the measurement signal.

However, these equipment from the state of the art are complex, and since their purpose is the measurement of the properties of the product "in natura", considering the extremely high absorption and the spreading of the illuminating radiation of the irradiated film, caused by the pigment particles, they need to operate with minute film thicknesses, which may reach the figures of 2 to 3 microns, requiring high power lamps, which leads to the heating of the sample, altering the density thereof and, consequently, the stability and preciseness of what it is intended to measure.

Other effects must also be added which are observed when trying to operate with film thicknesses in variable form to carry out colorimetric measurements by the transmission technique, such as: (a) effects related to environment pressure and temperature, which cause mechanical expansions and flexions in the measuring devices, leading to deviations in the transmittance results, limiting the use of the equipment; (b) instability in the calibration and in the maintenance of "zero thickness" between the optical surfaces of irradiation (optical windows), considering that the measuring of the thickness is carried out in an indirect manner, by means of a digital probe micrometer coupled to an indirect measuring rod, having a length that is thousands of times superior than the thickness which it is intended to measure, producing alterations in the thickness measurement data, both due to thermal factors related to the linear dilation coefficient of the rod material as due to mechanical flexion aspects.

In this manner, it is the object of the present patent of invention an equipment and method that enables the analysis of the fluid by means of a variable dilution between a paste and/or pigment dispersion, mineral fillers, or further a solution of dyes with a transparent vehicle, or further having controlled opacity, producing a homogeneous mixture that can be analyzed by means of the spectrophotometry technique by the transmission method, with a defined optical path (fixed thickness of the irradiated film), having the capacity of measuring properties such as the dyeing power, strength, covering and remaining colorimetric characteristics of a base or pigment paste.

DETAILED DESCRIPTION OF THE INVENTION

For the purposes of the present invention and in order to simplify, the expression "fluid for analysis" comprises pastes and/or pigment dispersions or mineral fillers; the expression "transparent vehicle and/or having controlled opacity" comprises a varnish and/or a mixture of solvents and/or resins and/or liquid vehicles with controlled opacity and/or combinations thereof, and may be presented in the context of the present invention as "vehicle"; the expression "analytical package" is used, for the purposes of simplification, to designate the mixture of fluid for analysis and the vehicle.

Figure 1:
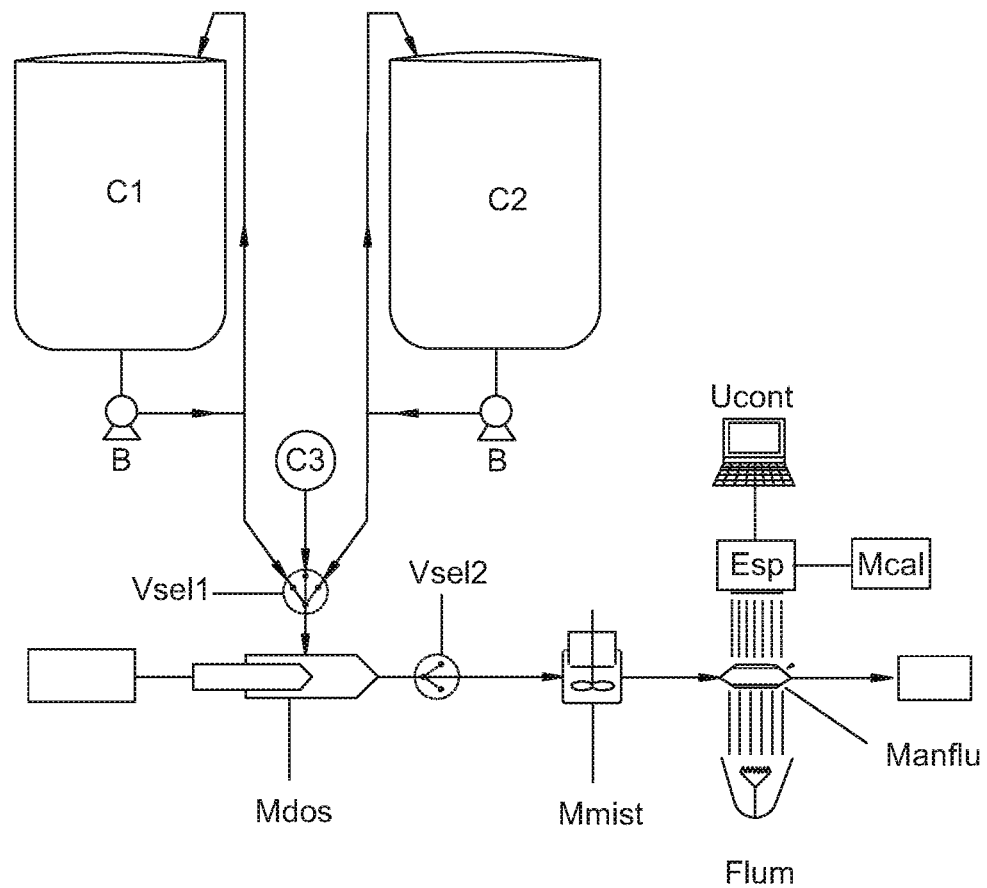
FIG. 1 presents a schematic representation of the constituent modules of the fluid analysis equipment.
Figure 2A:
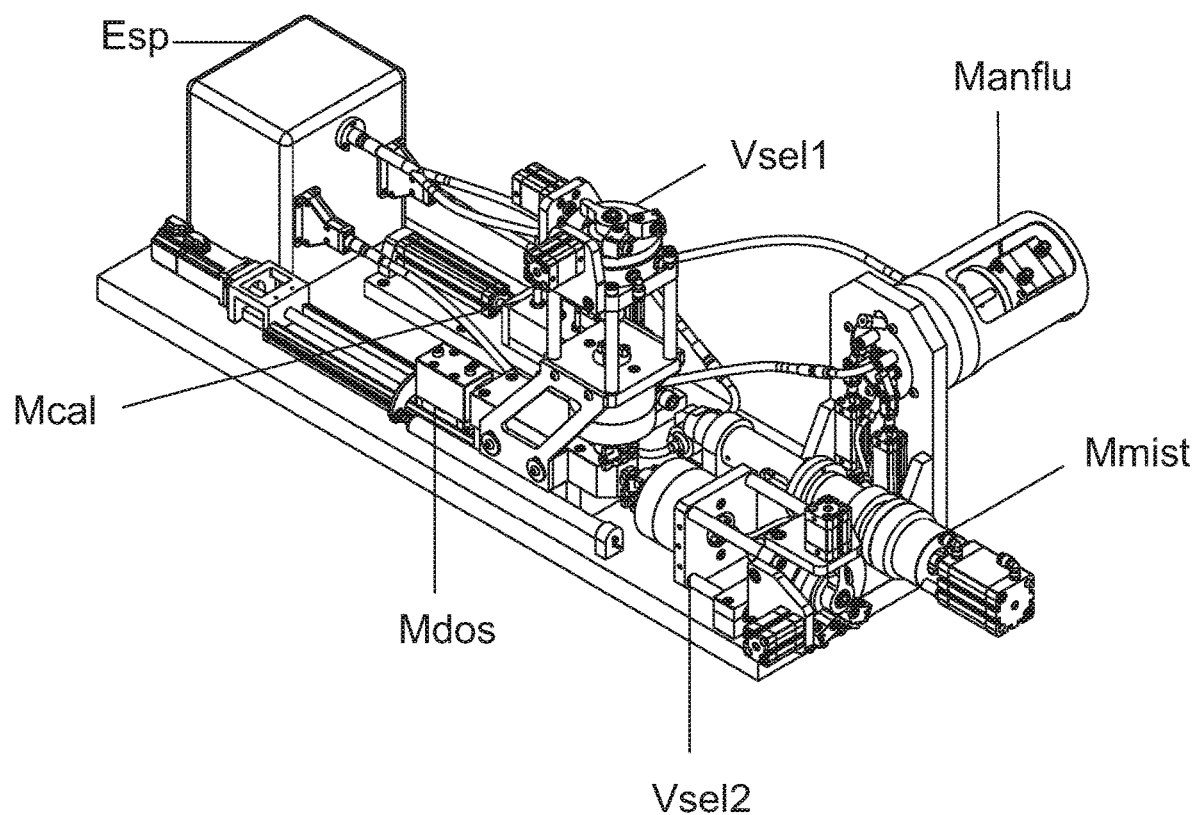
FIG. 2A presents a perspective view of the equipment that is the object of the present patent of invention and FIG. 2B presents a top view, evidencing the positioning of the modules.
Figure 2B:
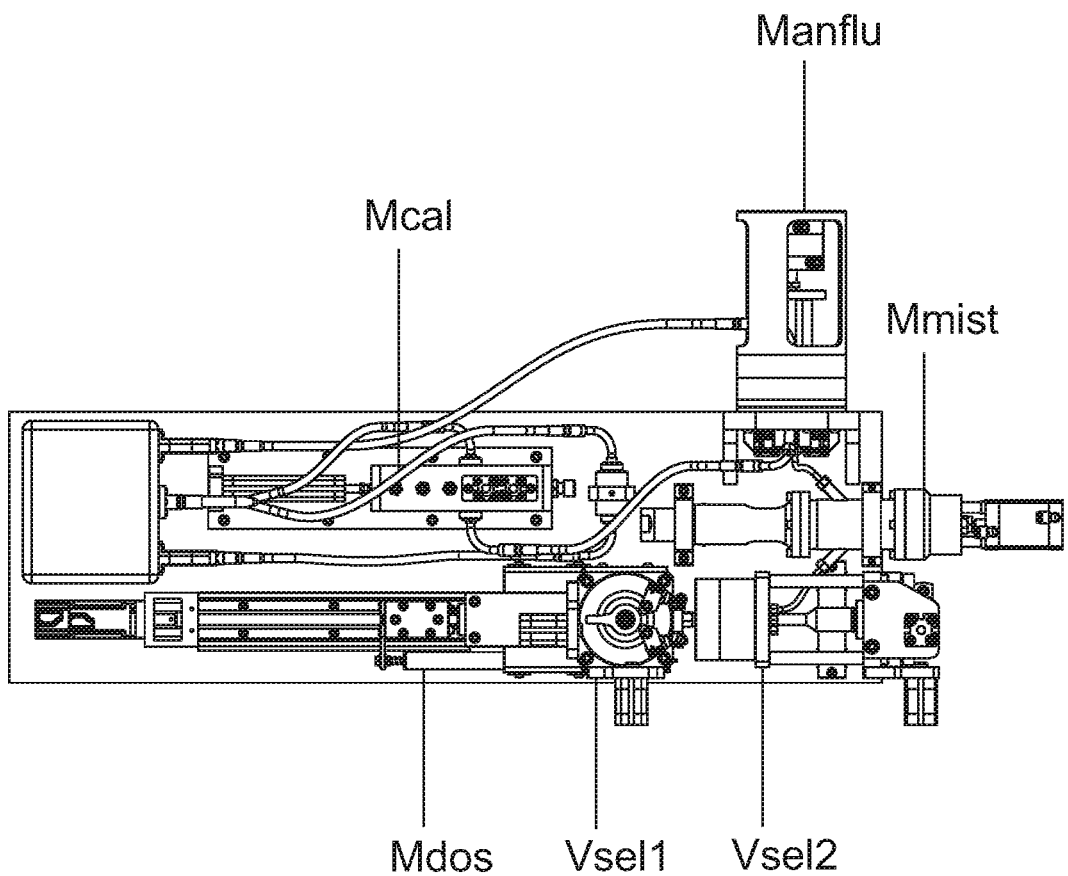
Figure 3A:
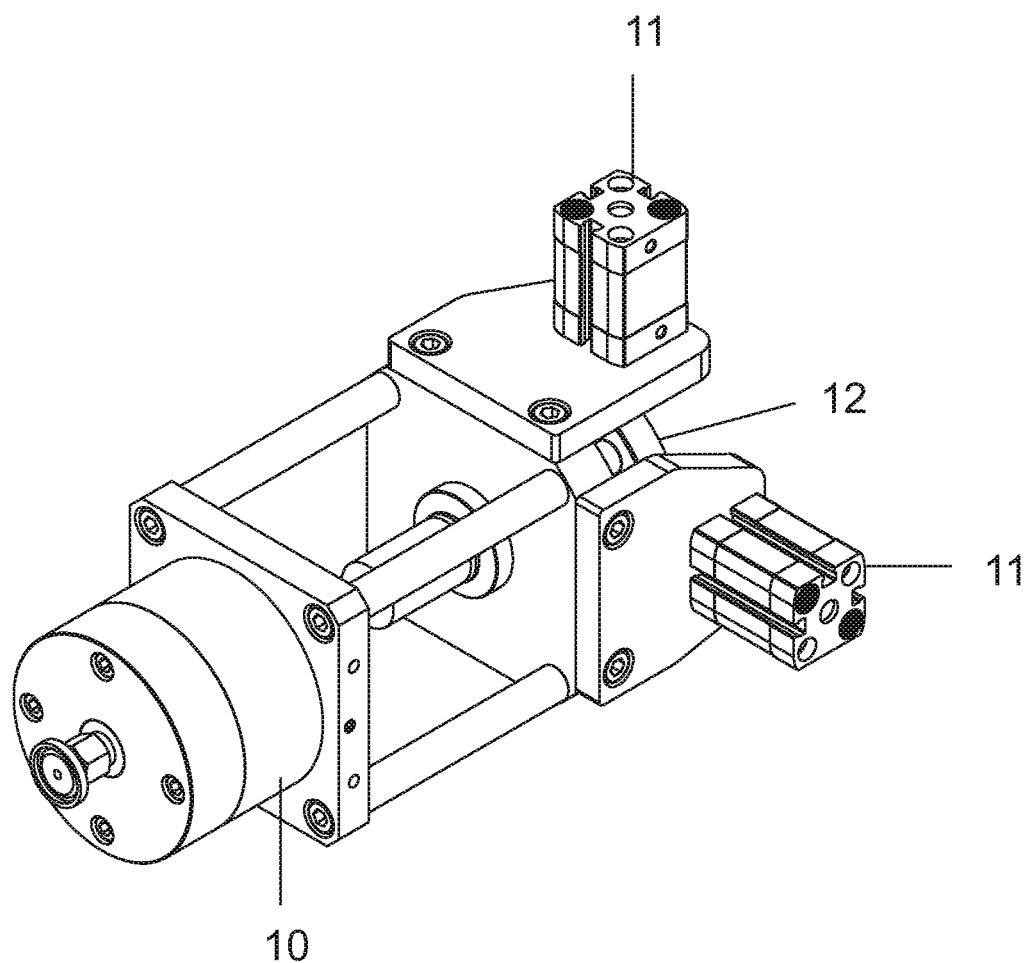
FIG. 3A presents a perspective view of the selector valve ($V_{sel1}$) and ($V_{sel2}$)
Figure 3B:
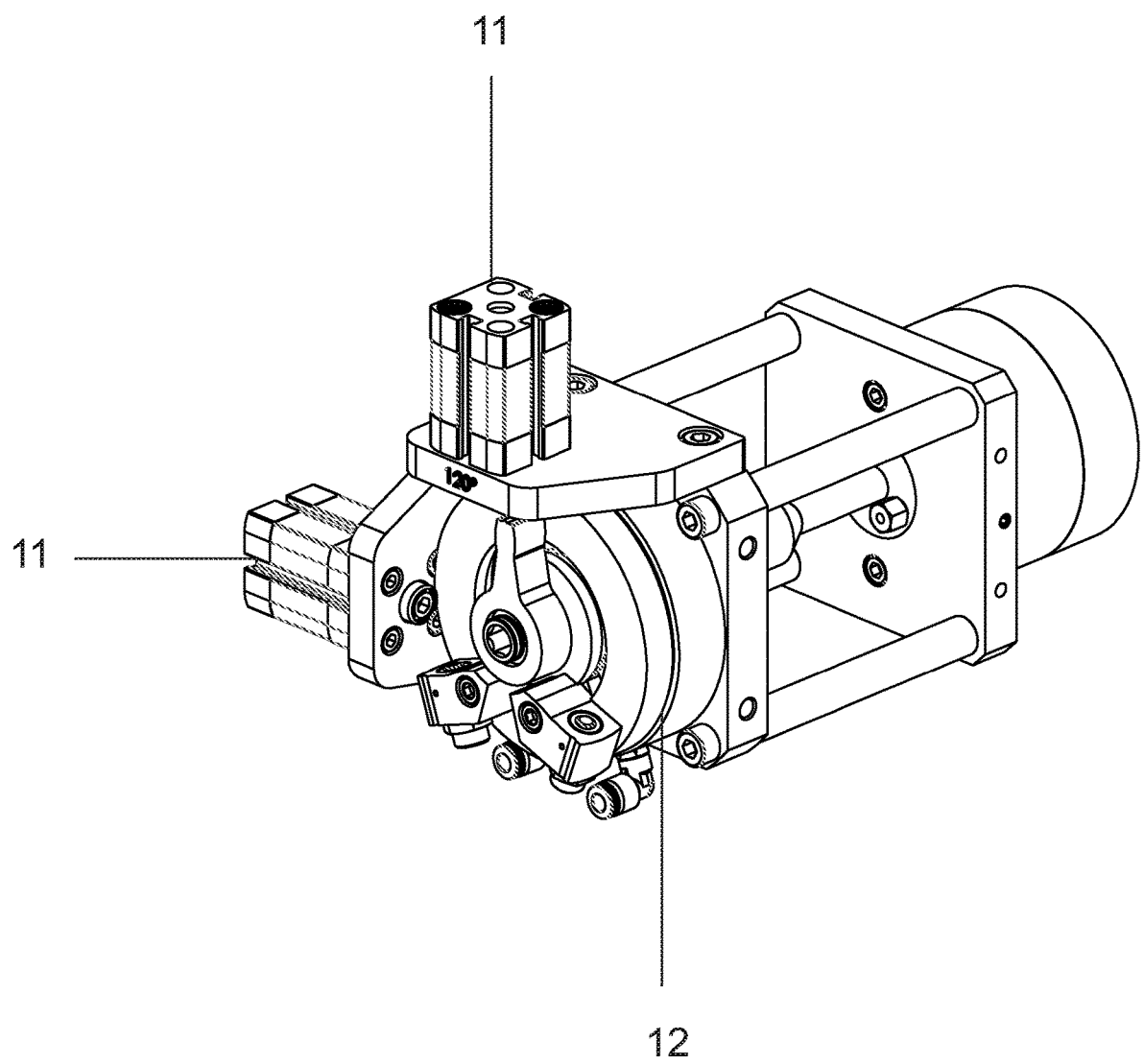
FIG. 3B presents a back view of the selector valve evidencing the pneumatic rotary actuator.
Figure 3C:
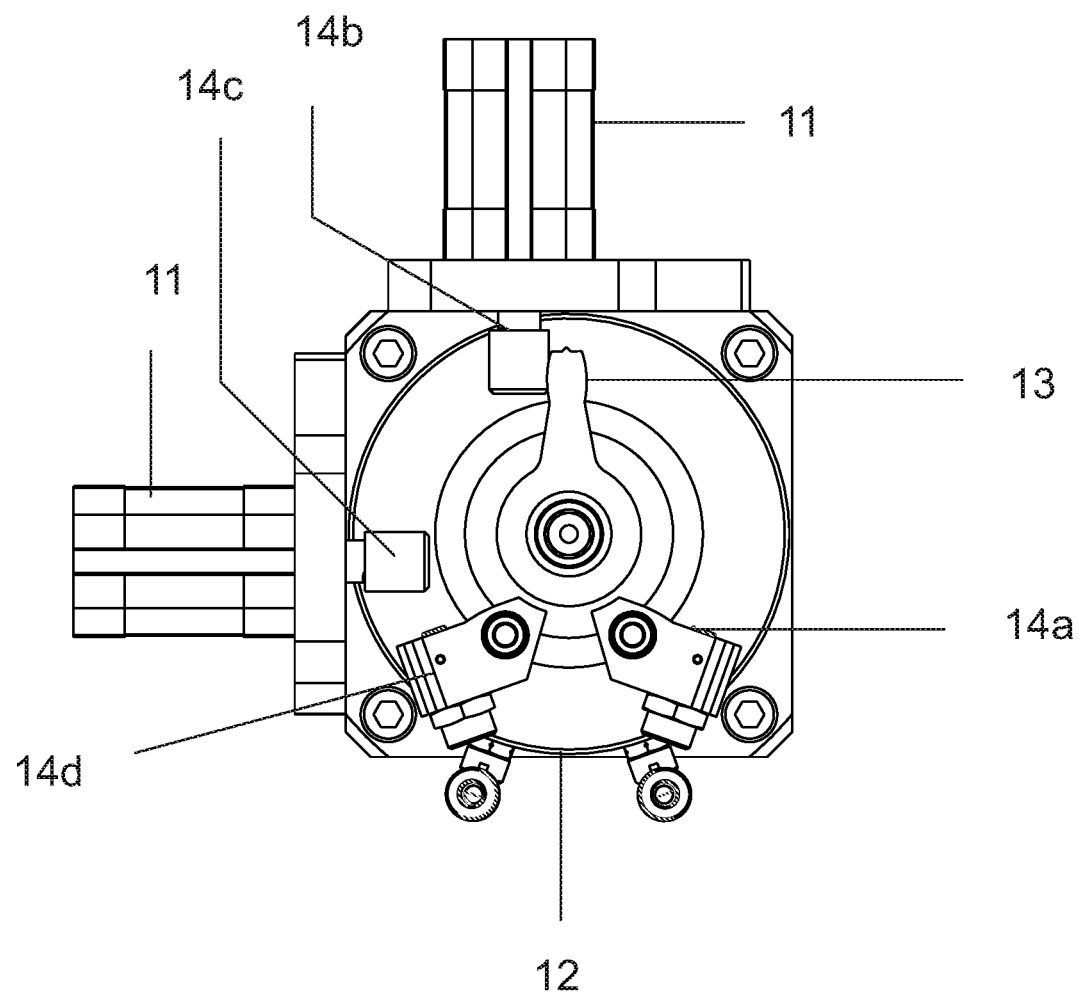
FIG. 3C presents a back view of the selector valve evidencing the pneumatic rotary valve actuator and the four stop points.
Figure 3D:
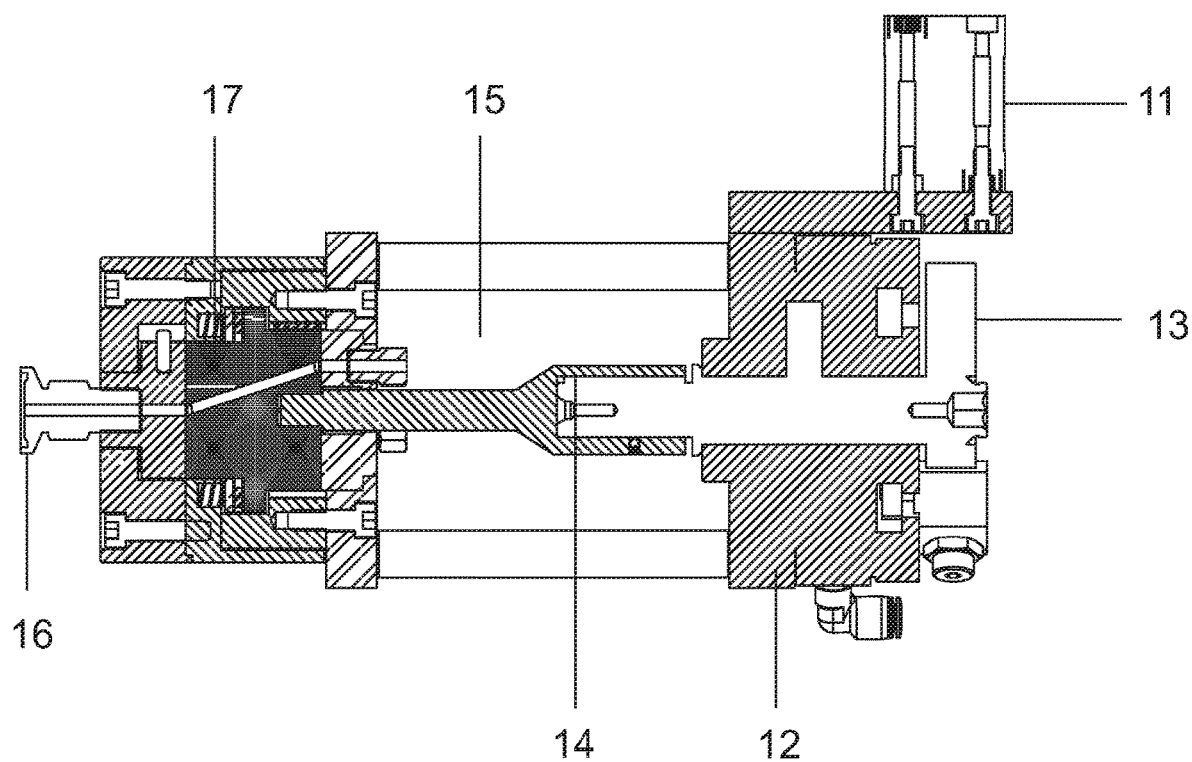
FIG. 3D presents a longitudinal sectional view.
Figure 3E:
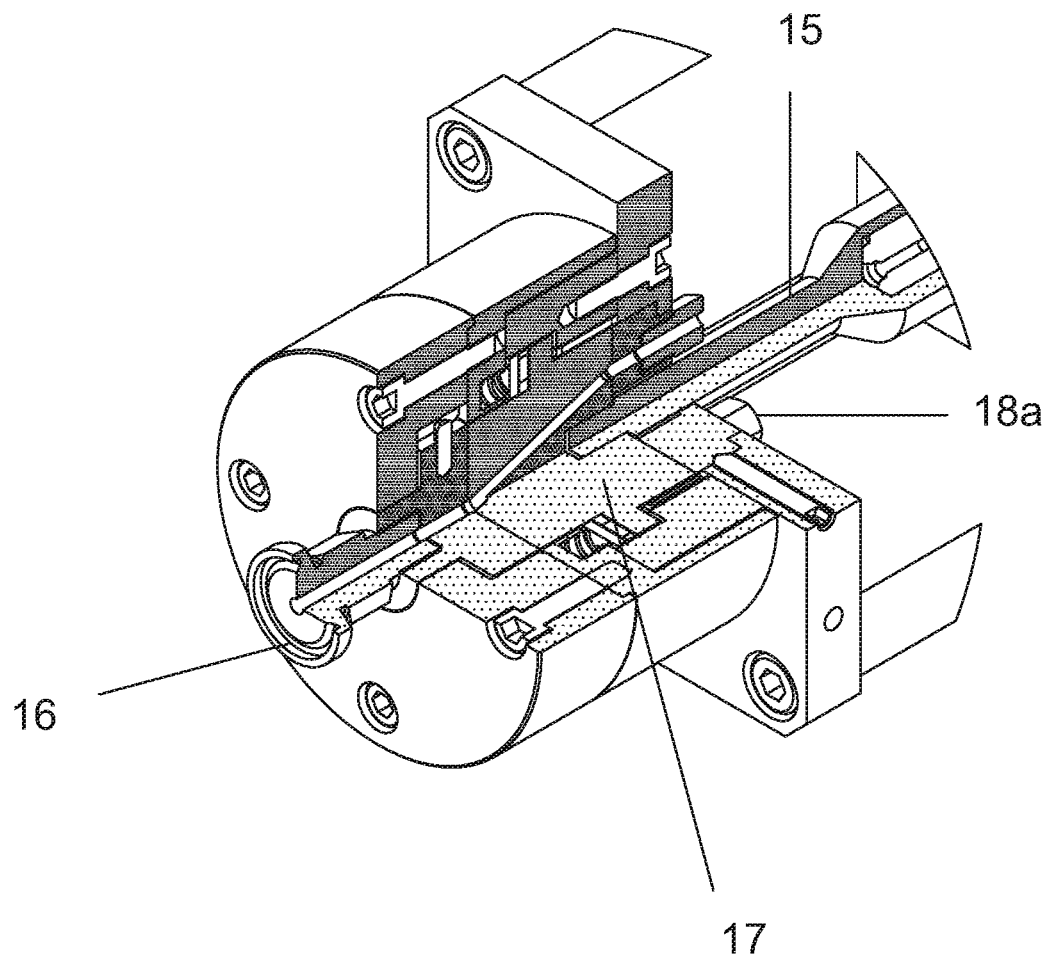
FIG. 3E presents a sectional perspective view of the selector valve body and the housing of the rotating valve head, having the channels for flow direction of the material to be distributed by the three distinct positions.
Figure 3F:
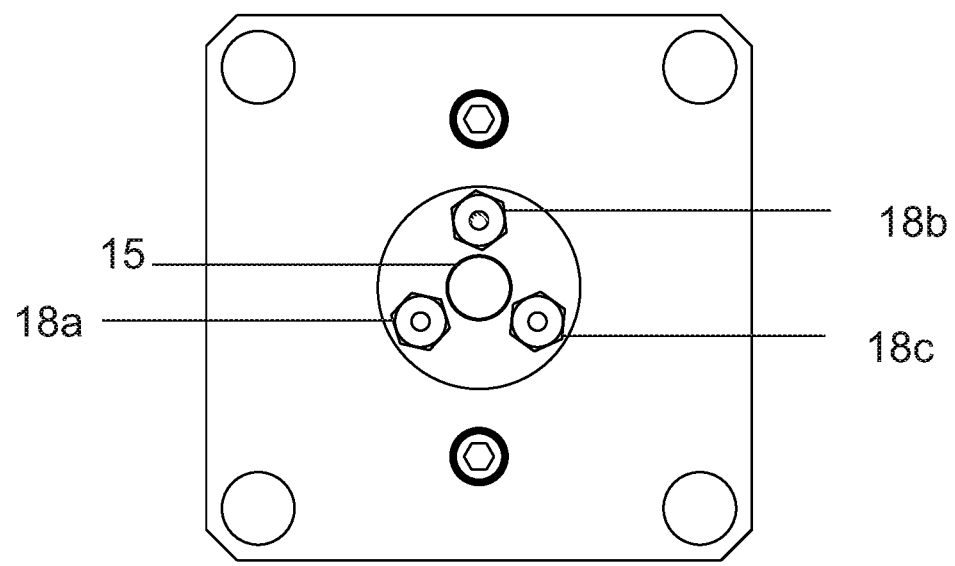
FIG. 3F presents the back part of the selector valve with the three connection entry and exit points.
Figure 4A:
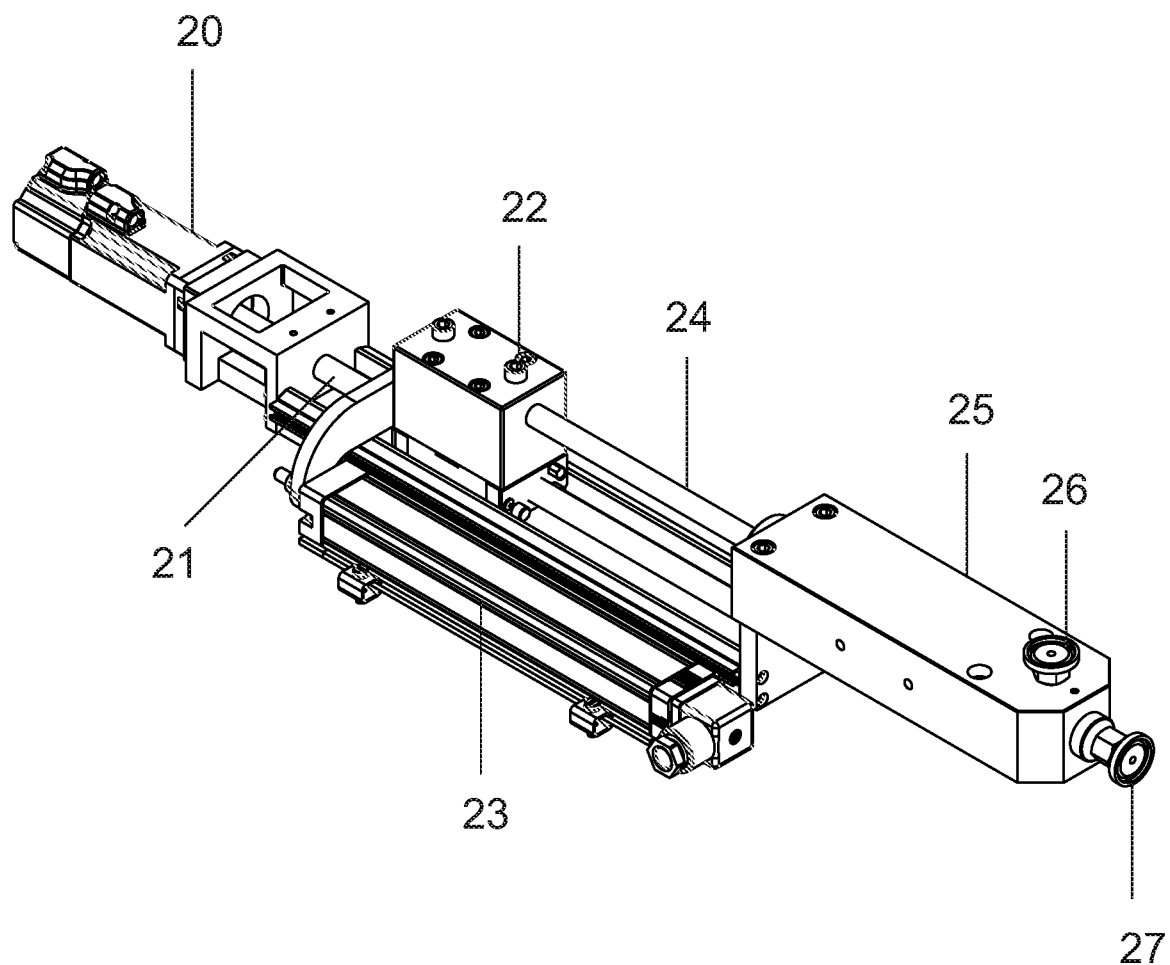
FIG. 4A presents a perspective view of the dosing module ($M_{dos}$)
Figure 4B:
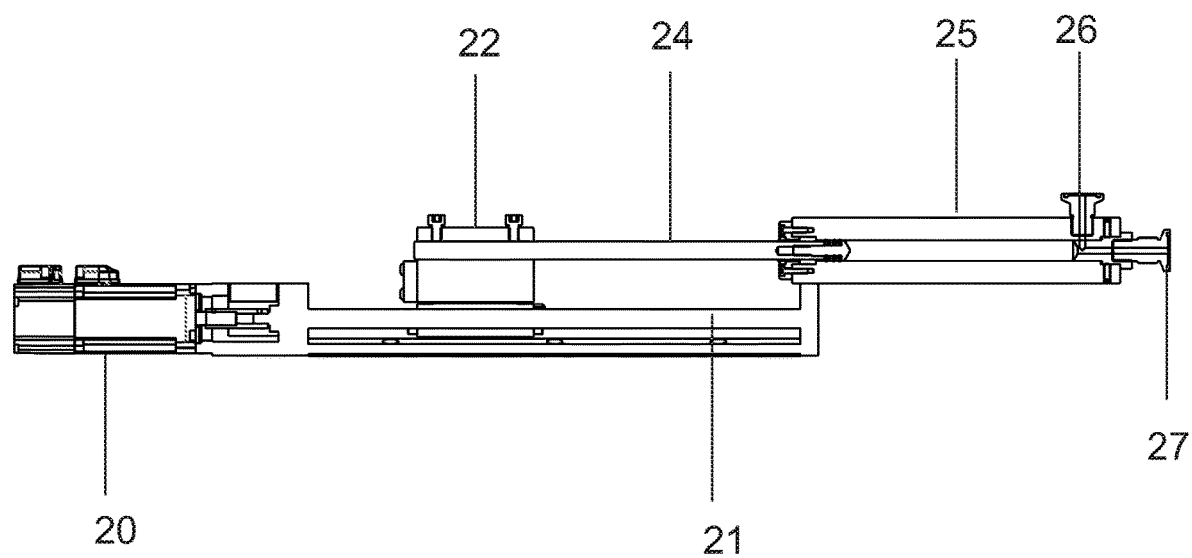
FIG. 4B presents a longitudinal sectional view and FIG. 4C presents the sectional details of the dosing volumetric syringe.
Figure 4C:
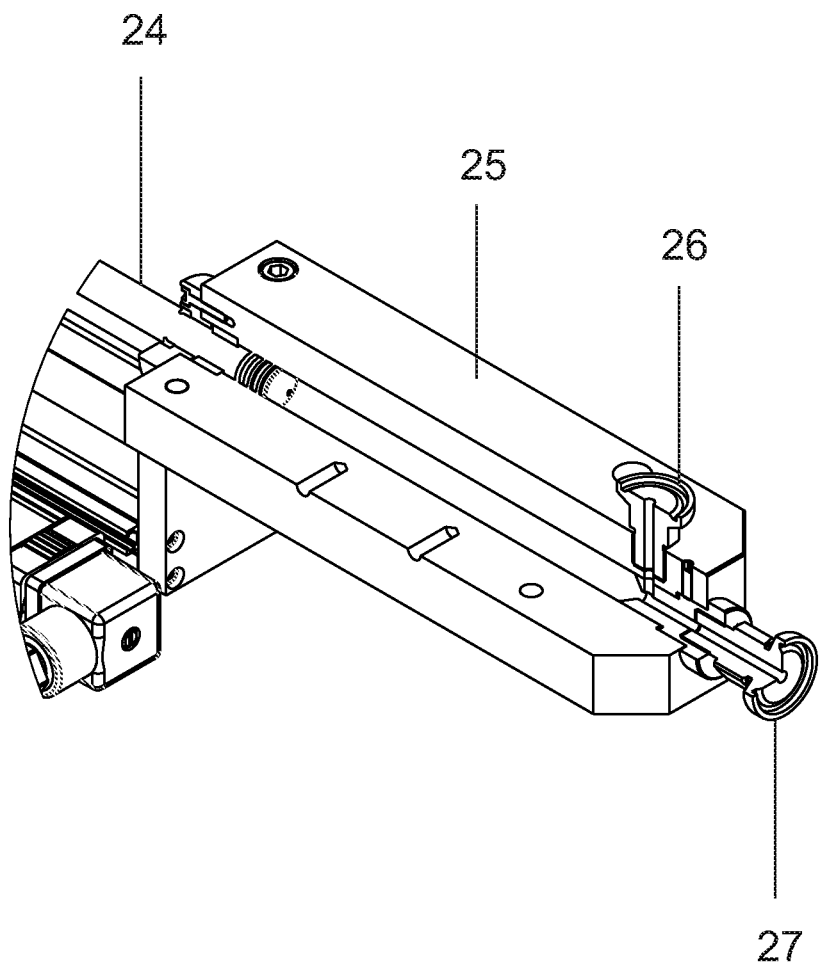

The equipment for analysis of a fluid that is the object of the present patent of invention, comprises a set of modules coupled in controlled series by a computer control unit ($U_{cont}$) which comprises a programmable microprocessor connected to a microcomputer, which schematic representation is presented in FIG. 1.

The equipment for analysis of a sample of fluid, suspension, dispersion, solution of dyes or a fluid emulsion presents a first selector ($V_{sel1}$) where the fluid to be analyzed, the vehicle, the solvent, respectively stored in containers (C1) and (C2) and (C3) are directed to the dosing module ($M_{dos}$).

The containers (C1) and (C2) are provided with pumps (B) for recirculation, of independent activation, which pressurize the admission points of the first selector valve ($V_{sel1}$) and that, consequently, feed a high-precision "dosing syringe" in the dosing module ($M_{dos}$) by means of control of the computer system by the control unit ($U_{cont}$) which, by means of algorithms, establishes the proportion between the fluid for analysis and the vehicle to be admitted to the interior of the dosing syringe of the dosing module ($M_{dos}$).

The fluid for analysis and the vehicle admitted in the dosing syringe by suction, in a proportion that is pre-defined by the computer system, are dislocated to the mixing module ($M_{mist}$) by means of moving the dosing syringe plunger by activating the motor of the linear positioner.

Between the dosing module ($M_{dos}$) and the mixing module ($M_{mist}$) there is provided a second selector valve ($V_{sel2}$) which, in the transference operation of the components of the dosing syringe from the dosing module ($M_{dos}$) to the mixing module ($M_{mist}$), is switched by the control unit ($U_{cont}$) to maintain the admission point in the "unblocked" position to allow the directional flow to the interior of the mixing module ($M_{mist}$), returning to the "blocked" position upon conclusion of the flow transfer.

In the mixing module ($M_{mist}$) the total load of the dosing syringe of the dosing module ($M_{dos}$) (fluid for analysis+vehicle or "analytical package"), after being unloaded to the interior thereof, is homogenized in a mixing chamber having a helical conical profile rotor connected to a high-speed pneumatic motor, controlled by the control unit ($U_{cont}$). Upon conclusion of the programmed mixing time, the total content of the mixing chamber is expelled to the interior of the fluid analysis module ($M_{anflu}$) by means of the displacement of the movable wall (plunger type), of the mixing chamber, connected to a pneumatic actuator, controlled by the control unit ($U_{cont}$).

In the fluid analysis module ($M_{anflu}$) a film is formed of the homogenized fluid in the mixing module ($M_{mist}$), said film being irradiated by means of a luminous source ($F_{lum}$) and analyzed by a spectrophotometer (Esp), by means of the spectroscope technique by the transmission method, in the spectral region comprised between 100 and 6000 nanometers (from the radiation contained in the region of the ultraviolet to the radiation range contained in the infrared region), providing, in this manner, a precise determination of the characteristics related to the concentration and/or energy absorption index in the spectral region defined and/or transparency and/or covering and/or dyeing power (strength) and remaining colorimetric characteristic, providing information for adjustments of these properties.

For the calibration of the spectrophotometer, there is provided an optical calibration module ($M_{cal}$) which introduces in the sample channel a set of "neutral optical filters" having known attenuation, which blocks part of the luminous radiation that reaches the detector of the spectrophotometer, avoiding the "saturation" thereof during the calibration phase. This methodology applied to samples having extremely high luminous radiation absorption (opaque liquids and/or highly filled with pigments or solid blocking particles) further foresees that, during the sample analysis phase, the attenuating filter is removed in an automatic manner, enabling the incident luminous radiation to have an extremely high intensity (multiplied by the filter attenuation factor), in this manner obtaining a quantity of radiation emerging from the sample in optimal energy levels for the detector, where the relation signal/sound is very low, propitiating in this manner measurements in optimal levels, where the measurement data collected by the spectrophotometer, by means of a subsequent mathematical treatment, are then divided by the "neutral optical filter attenuation index", in each wavelength, obtaining in this manner the real transmission data, whereby the same may have extremely low values, however, with extremely high precision.

As presented in FIGS. 3A to 3F, the first selector valve ($V_{sel1}$) presents a rotating flange (17) with movement executed by means of a rotary pneumatic actuator (12), said rotating flange (17) which presents four stop positions (14a), (14b), (14c) and (14d), having their positioning controlled by the control unit ($U_{cont}$), where each stop position implies in a set of commands that are previously programmed by the control unit ($U_{cont}$). The stop points (14a) and (14d), are regulable stops of the rotary pneumatic actuator itself (12), while the stop positions (14b) and (14c) are defined by stops that are commanded by two auxiliary pneumatic actuators (11).

In this first selector valve ($V_{sel1}$), a first stop position (14a) allows the admission of the fluid for analysis deposited in the container C1 at the admission point (18a) of the first selector valve ($V_{sel1}$), a second stop position allows the admission of the vehicle deposited in the container C2 at the admission point (18b) of the first selector valve ($V_{sel1}$), a third stop position allows the admission of the cleaning solvent stored in container C3 at the admission point (18c) of the first selector valve ($V_{sel1}$) and a fourth stop position promotes the blocking of the passage of fluid in all directions.

The admission of fluids at the admission point of the first selector valve ($V_{sel1}$) is made by suction generated from the pressurization carried out by the pumps (B) of the containers C1 and C2.

The stop position that allows the passage of the solvent will be sufficiently detailed throughout the present specification.

At the beginning of the analytical process, the control unit ($U_{cont}$), by identifying the first stop position (14a) by means of sensors installed in the rotary pneumatic actuator (12), aligns the exit from container C1 with the admission point (18a) of the first selector valve ($V_{sel1}$), admitting the entry of fluid for analysis at the admission point of the first selector valve $V_{sel1}$), in the proportion defined by the control unit ($U_{cont}$), to forward the fluid for analysis to the interior of the dosing syringe in the dosing module ($M_{dos}$). In the plunger (24) of the dosing syringe (25) there is provided a linear positioner (21) activated by a motor (20) which retreats said plunger (24) until the volume of fluid for analysis defined by the computer program installed in the processor of the control unit ($U_{cont}$) is reached, the contents of the fluid for analysis being admitted, measured in an indirect manner by means of a linear transducer (23), connected to the plunger (24).

The control unit ($U_{cont}$), by identifying the second stop position (14) by means of the spin of the rotary pneumatic actuator (12), aligns the exit of container C2 with the admission point of the first selector valve ($V_{sel1}$), admitting the entry of the vehicle at the admission point (18b), of the first selector valve ($V_{sel1}$), in the proportion defined by the control unit ($U_{cont}$), to forward the vehicle to the interior of the dosing syringe of the dosing module ($M_{dos}$). In the plunger (24) of the dosing syringe (25) there is provided a linear positioner (21), actuated by a motor (20) which retreats the plunger of the said syringe (24) until the volume of the vehicle defined by the computer program installed in the processor of the control unit ($U_{cont}$) is reached, the content of the vehicle being admitted measured in an indirect manner by means of a linear transducer (23), connected to the plunger (24), in this manner completing the total volume of the syringe, named "analytical package" and having high volumetric precision.

When the fluids of the "analytical package" are being carried to the interior of the dosing syringe (25) of the dosing module ($M_{dos}$), the control unit ($U_{cont}$) maintains the stop position of the said second selector valve ($V_{sel2}$) in the blocked position (14d), preventing the passage or leakage of fluid to the mixing module ($M_{mist}$).

Once transferred to the interior of the dosing syringe (25) the components of the fluid formulation (analytical package), the control unit ($U_{cont}$) activates the rotary pneumatic actuator (12) of the first selector valve ($V_{sel1}$) until the fourth stop position (14d), totally blocking the passage of fluid to the dosing module ($M_{dos}$).

When the passage of fluid to the dosing module ($M_{dos}$) is blocked by the positioning of the first selector valve ($V_{sel1}$) to the stop point (14d), the control unit ($U_{cont}$) then positions the selector valve ($V_{sel2}$), by means of the rotary pneumatic actuator (12) to the position of direct connection between the dosing module ($M_{dos}$) and the mixing module ($M_{mist}$), in a similar manner to the procedures previously described for the first selector valve ($V_{sel1}$).

Figure 5A:
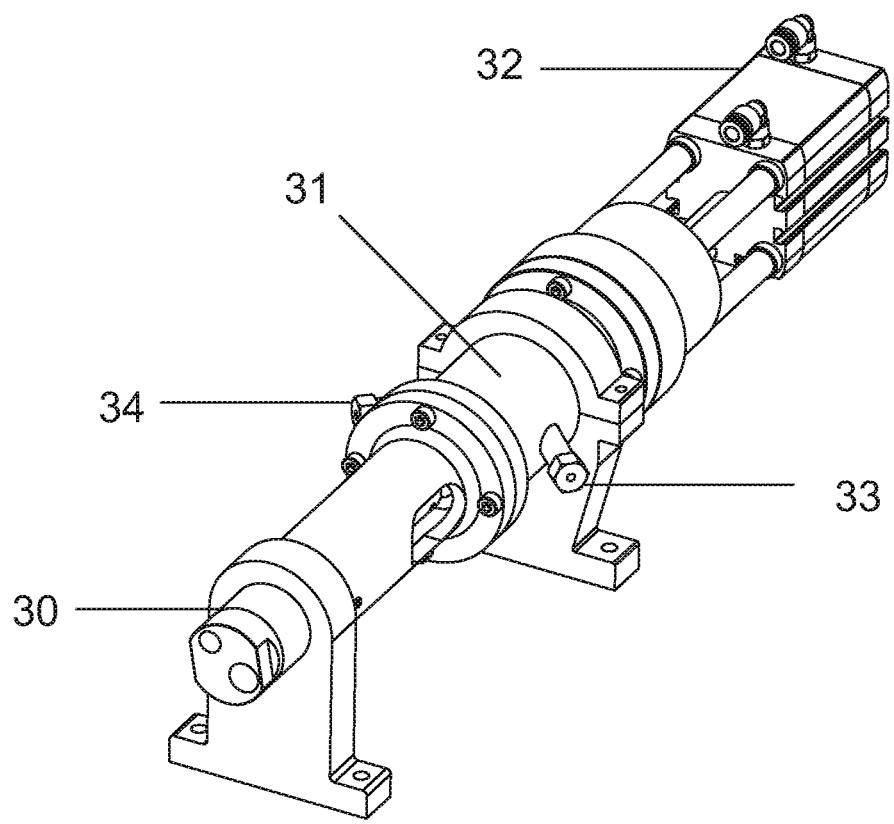
FIG. 5A presents a perspective view of the mixing module ($M_{mist}$)
Figure 5B:
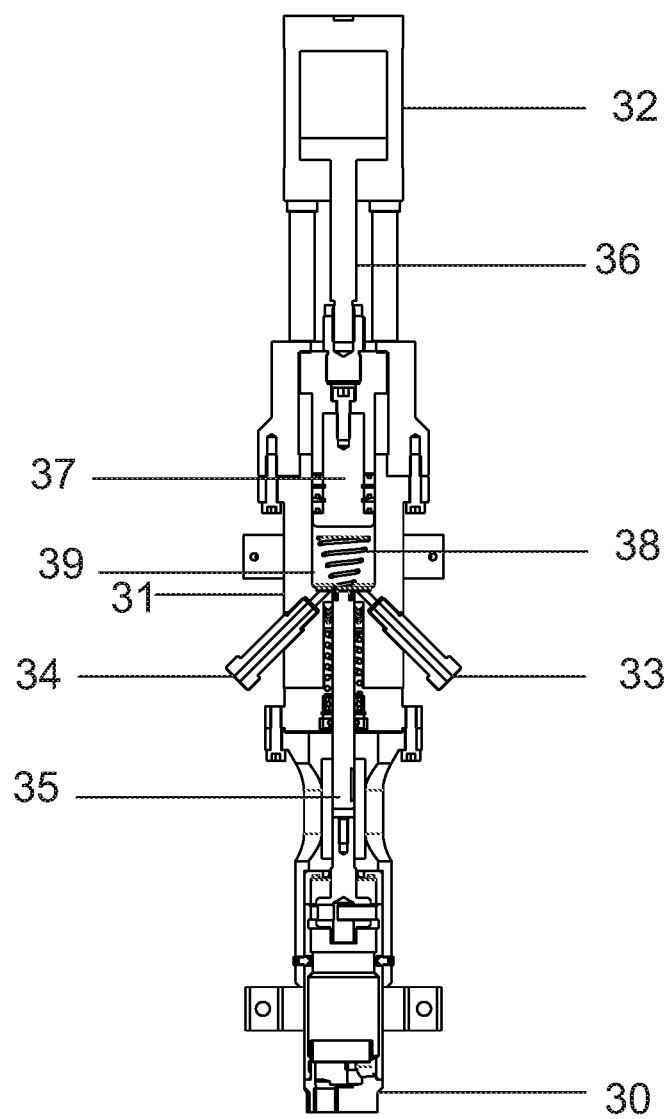
FIG. 5B presents a longitudinal sectional view.
Figure 5C:
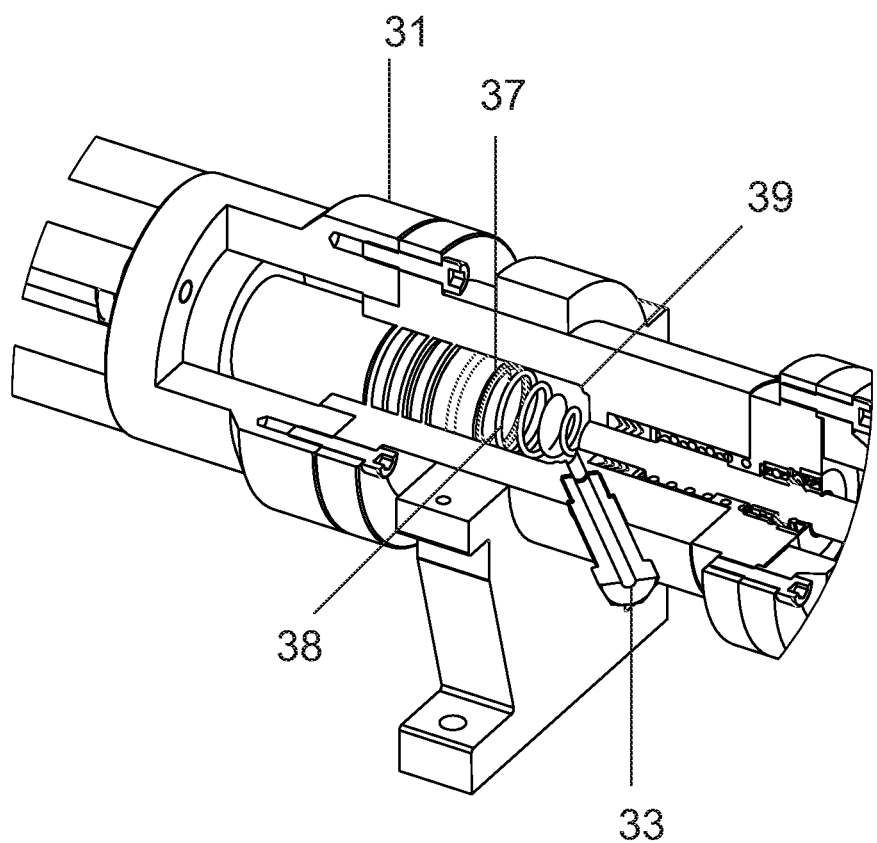
FIG. 5C presents a perspective view with sectional details of the variable chamber in homogenization mode.
Figure 5D:
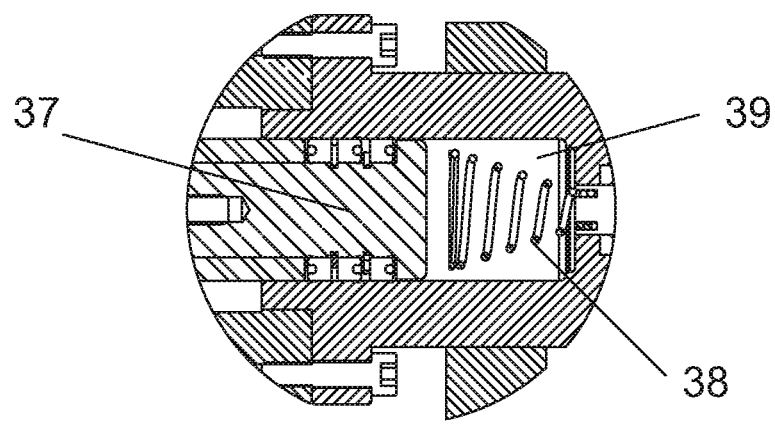
FIG. 5D presents the detail of the variable chamber in the homogenization mode and FIG. 5E presents the detail of the variable chamber in the product expulsion mode.

The control unit ($U_{cont}$) then activates the motor (20) which dislocates the plunger (24) of the dosing syringe (25) forward, to expel the total contents of the "analytical package" stored in the interior of the syringe (25) towards the inner chamber (39) of the mixing module ($M_{mist}$), which will be in the (expanded chamber) mode, as presented in FIG. 5D, whereby all this displacement of fluid is monitored by the linear transducer (23) connected to the plunger (24) of the dosing syringe (25).

Once concluded the dislocation of the plunger (24) of the dosing syringe (25), when the mixing chamber (39) of the mixing module ($M_{mist}$) will be completely filled, the control unit ($U_{cont}$) then switches the second selector valve ($V_{sel2}$) to the blocked position (14d), as previously described.

The next step of the process is described as the mixing and homogenization phase of the "analytical package" in the interior of the mixing chamber (39) of the mixing module ($M_{mist}$).

In this step, the control unit ($U_{cont}$), after detecting the blocking of the second selector valve ($V_{sel2}$), commands the pneumatic motor (30) which, by means of an axis (35) connected on one side to the pneumatic motor (30) and on the other side to a helical conical agitator (38), to effect the spin in high rotation for a pre-determined time interval, which time is sufficient to promote the complete homogenization of the contents of the mixing chamber (39).

Upon conclusion of the homogenization step, the control unit ($U_{cont}$) commands the expulsion of the content of the mixing chamber (39) directly to the interior of the property measurement cell (49) of the fluid analysis module ($M_{anflu}$).

This transference of the homogenized "analytical package" is carried out by means of the exit connector (34) of the mixing module ($M_{mist}$) which connects itself by means of specific piping to the entry connector (41) of the fluid analysis module ($M_{anflu}$).

Figure 5E:
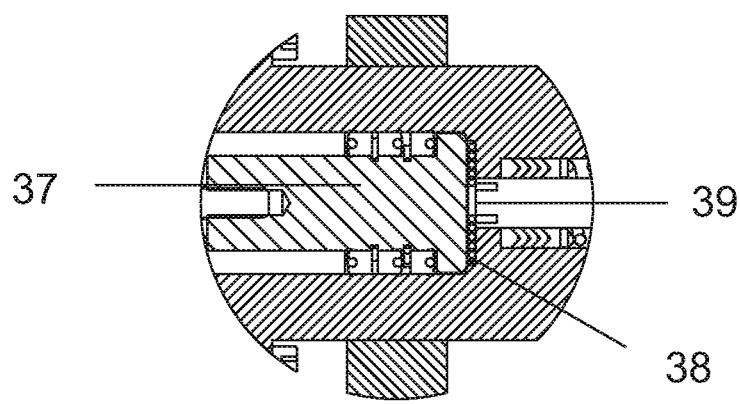

During this cycle of transference to the interior of the fluid analysis module ($M_{anflu}$), the control unit ($U_{cont}$) will activate the mover pneumatic actuator (32), which is connected to the movable wall of the inner chamber (37) of the mixing module ($M_{mist}$), moving it forward until all the content of the inner chamber (39) is expelled and transferred to the fluid analysis module ($M_{anflu}$), as evidenced in FIG. 5E.

In this step, the helical conical type agitator (38) acts as a spring, being totally compressed without opposing or creating any restriction to the integral expulsion of the material contained in the mixing chamber (39).

Figure 6A:
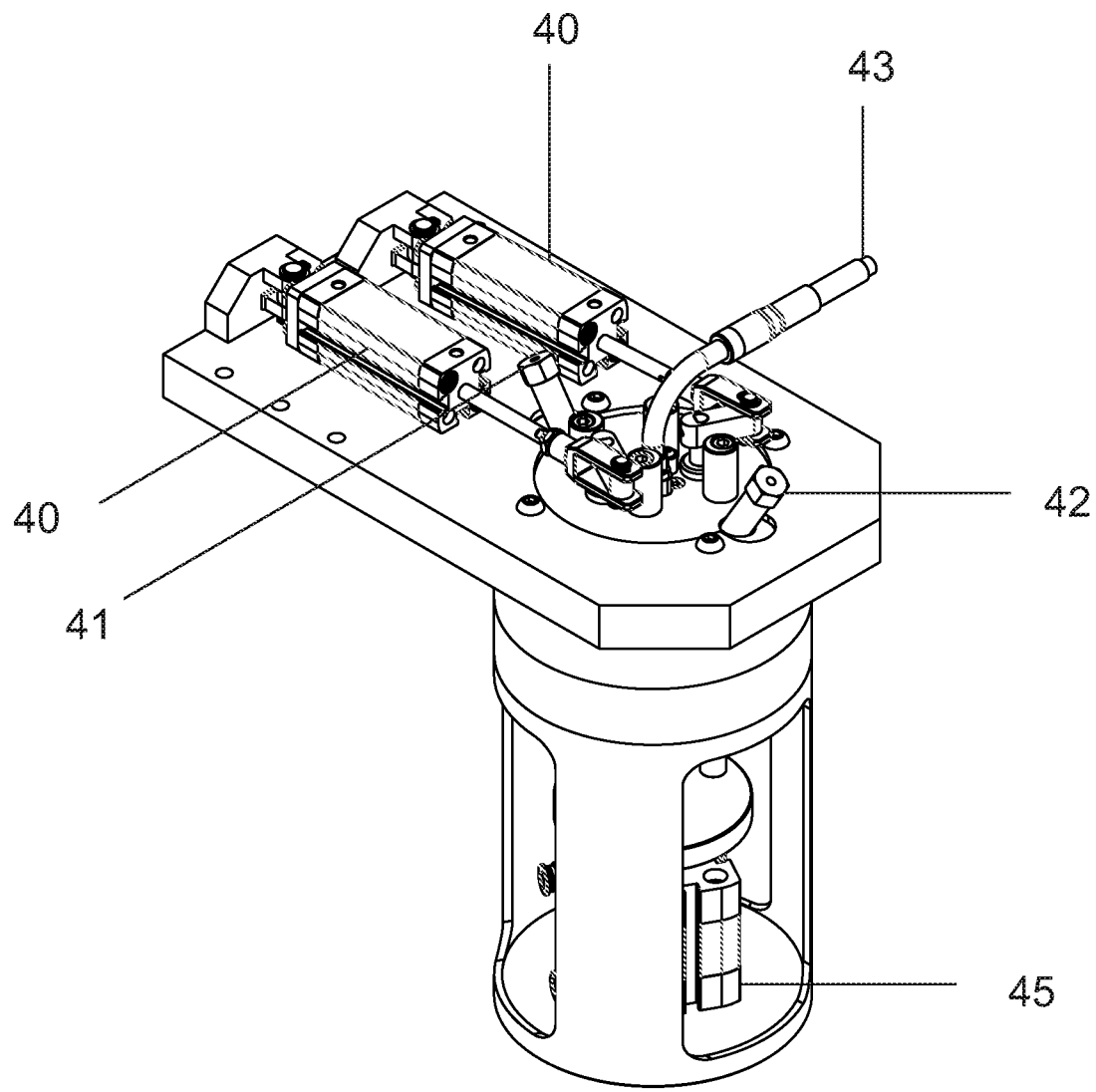
FIG. 6A presents a perspective view of the fluid analysis module ($M_{anflu}$)
Figure 6B:
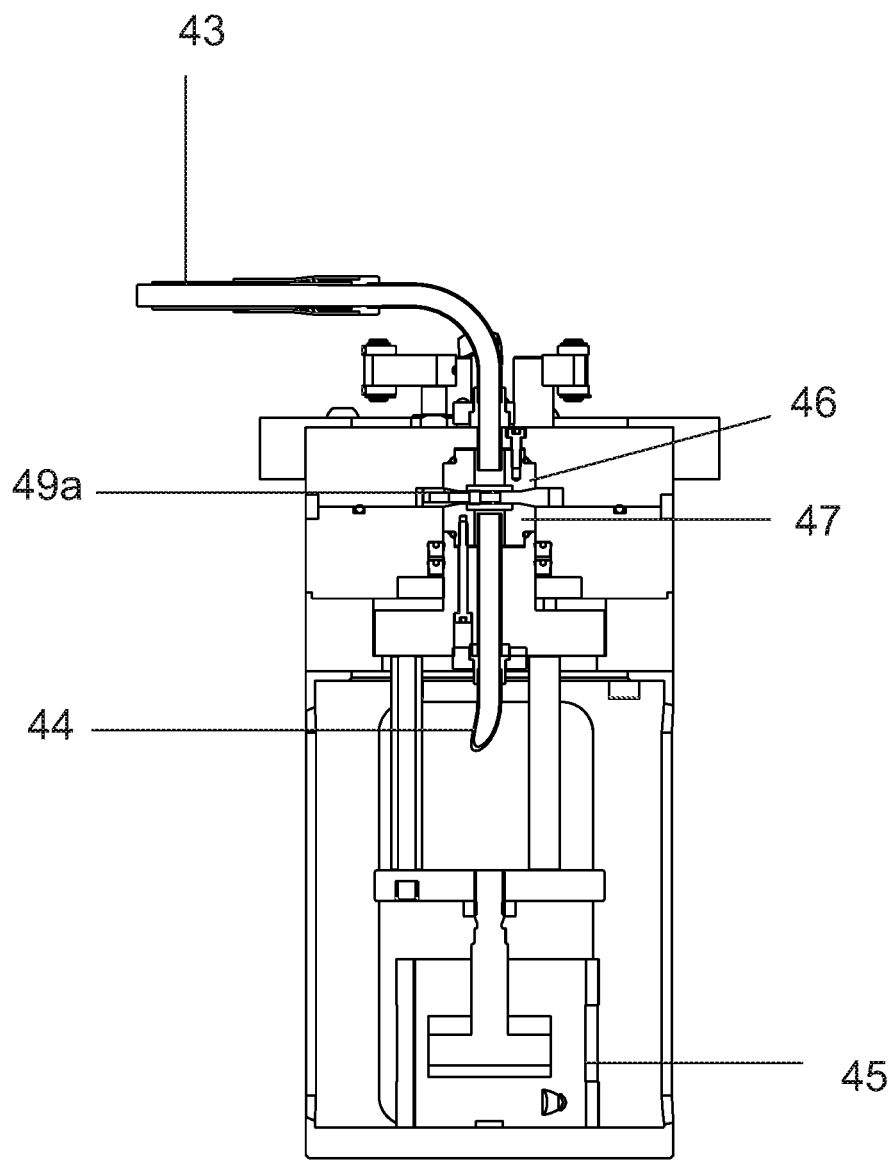
FIG. 6B presents a sectional view.
Figure 6C:
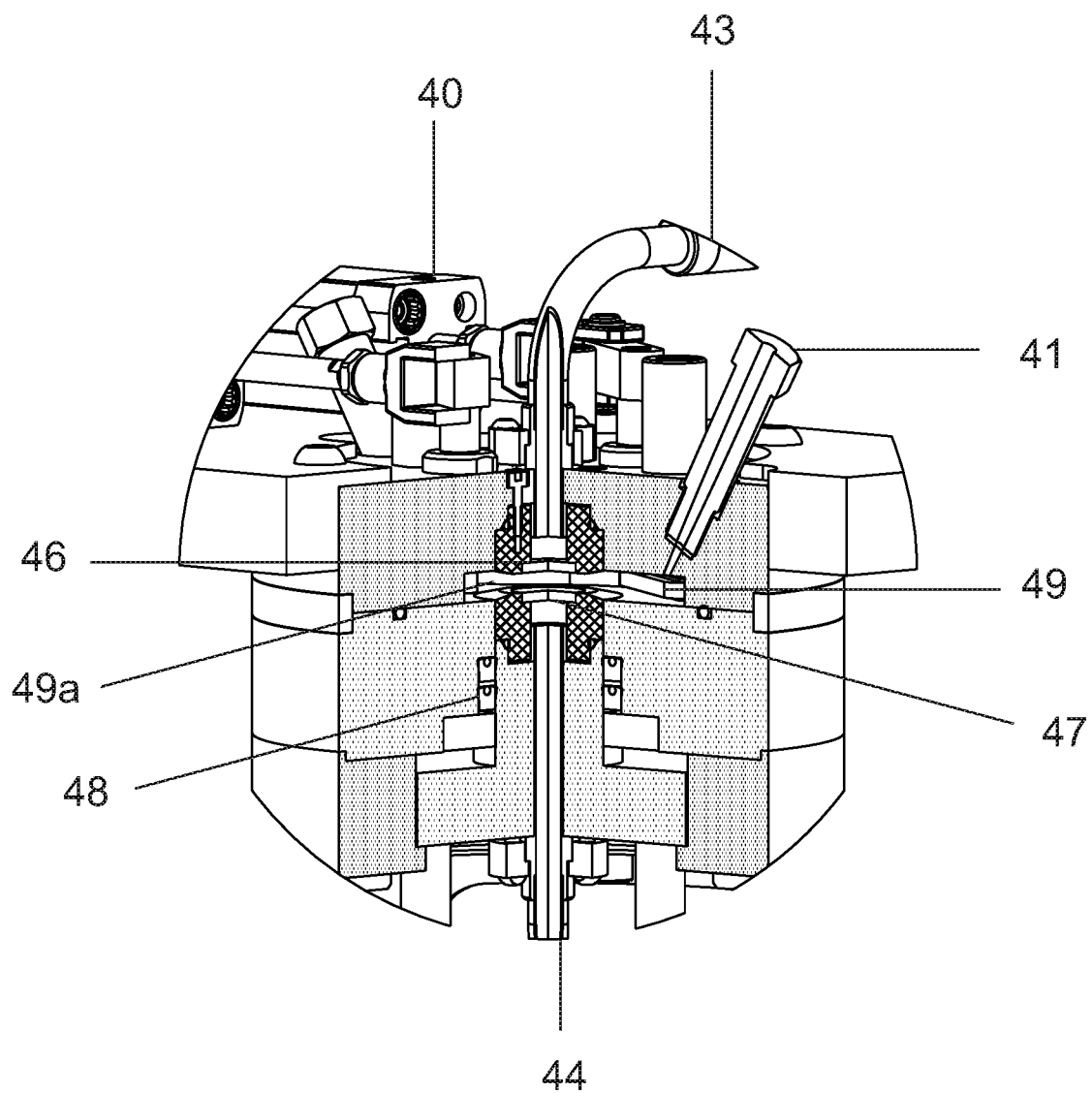
FIG. 6C presents the sectional detail of the internal elements.
Figure 6D:
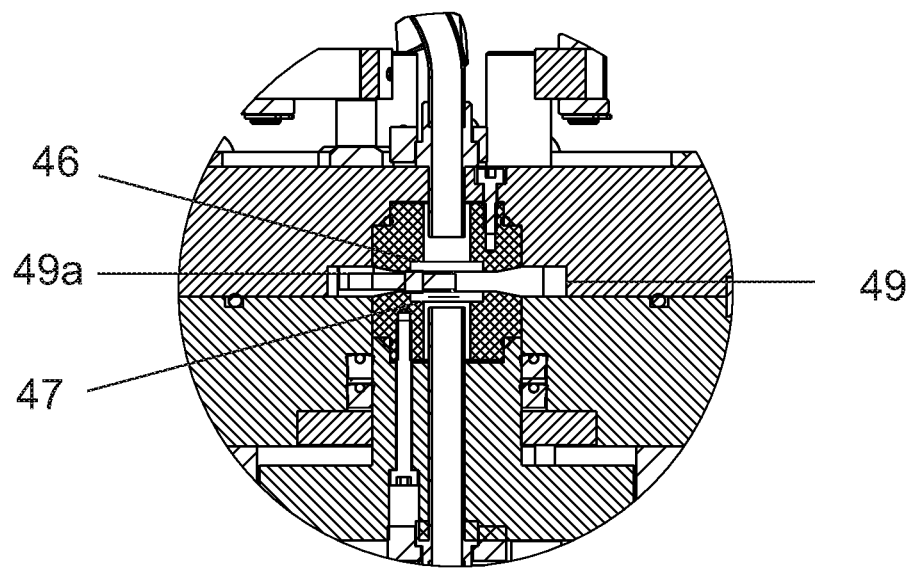
FIG. 6D presents a sectional view of the reading chamber in the cleaning/product admission mode.

In the subsequent step, the control unit ($U_{cont}$) monitors the positioning of the interior of the analytical chamber (49a), whereby during all the transference phase, the analytical chamber (49a) must be in the expanded mode, according to FIG. 6D, and for this the pneumatic positioning actuator (45) must be completely retreated, allowing maximum spacing between the static optical window (46) and the movable optical window (47), not occurring any resistance of the fluid in totally filling in the reading cell cavity (49a), further expelling the sample of the "analytical package" of the previous analysis cycle.

Figure 6E:
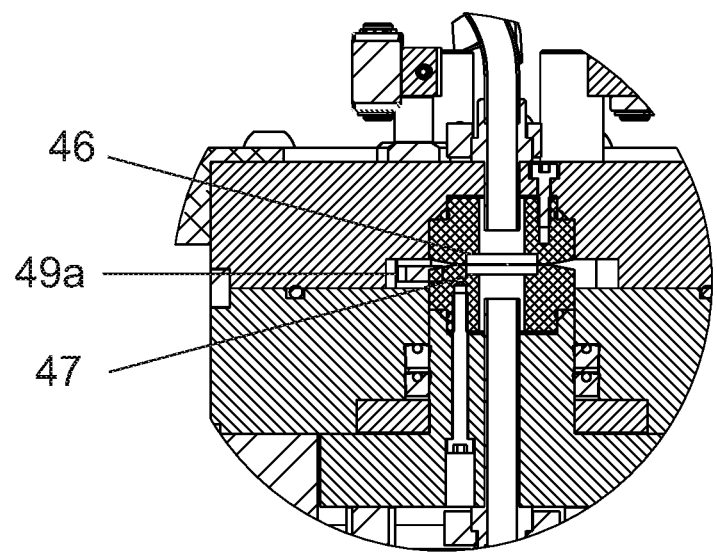
FIG. 6E presents a sectional view of the reading chamber with the "optical windows" in the fixed analytical spacing for reading of the properties of the fluid that is being analyzed.
Figure 6F:
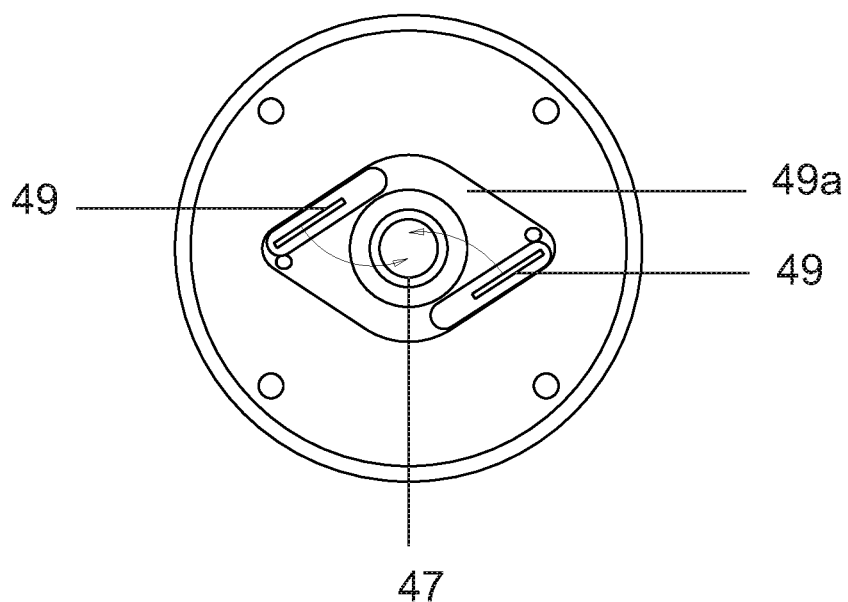
FIG. 6F presents a top view of the inner part of the reading chamber presenting the centralized positioning of the "optical window" measurement and further the two cleaning pallets of the surfaces of the reading "optical windows"
Figure 6G:
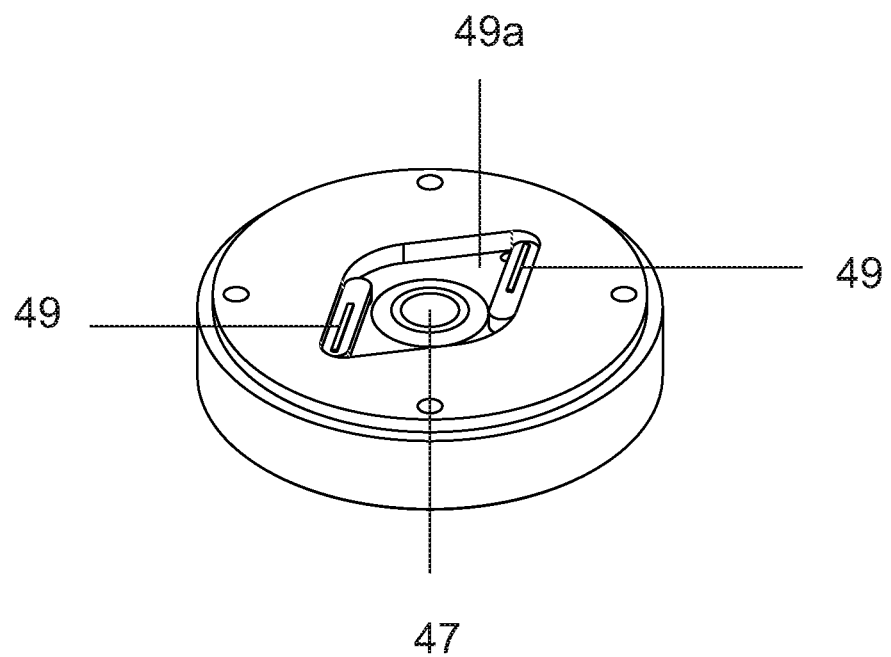
FIG. 6G presents a perspective view of the measurement chamber.
Figure 6H:
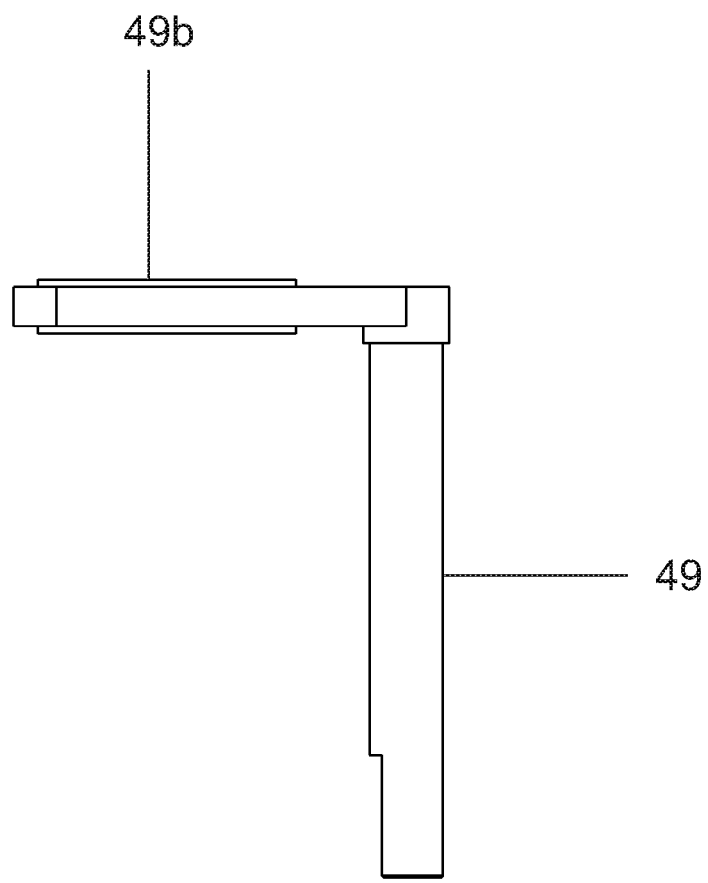
FIG. 6H presents a side view of the mechanical cleaning arm of the optical windows.
Figure 6I:
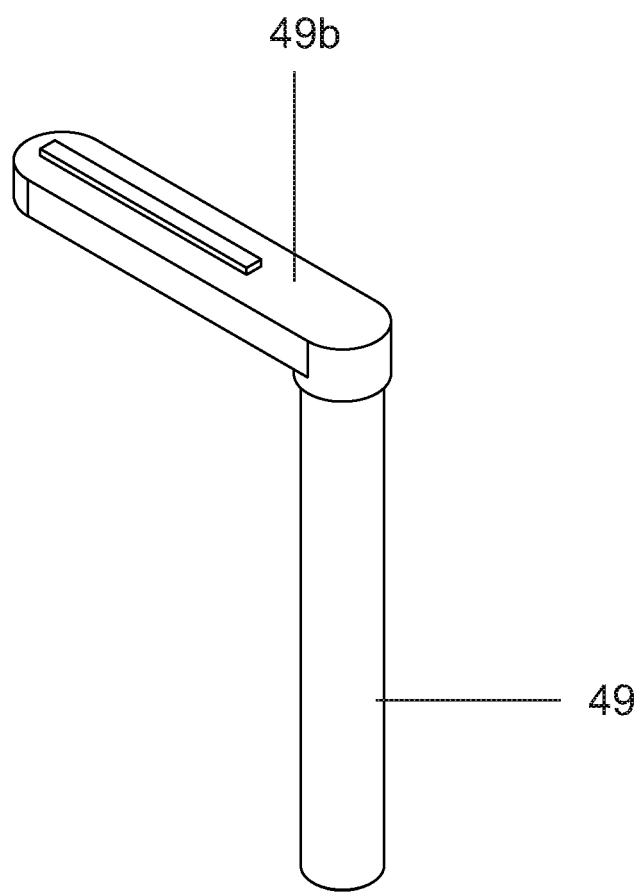
FIG. 6I presents a perspective view of the mechanical cleaning arm of the optical windows and FIG. 6J presents sectional details of the interior of the cavity of the measurement cell with emphasis on the cleaning pallets of the optical windows.
Figure 6J:
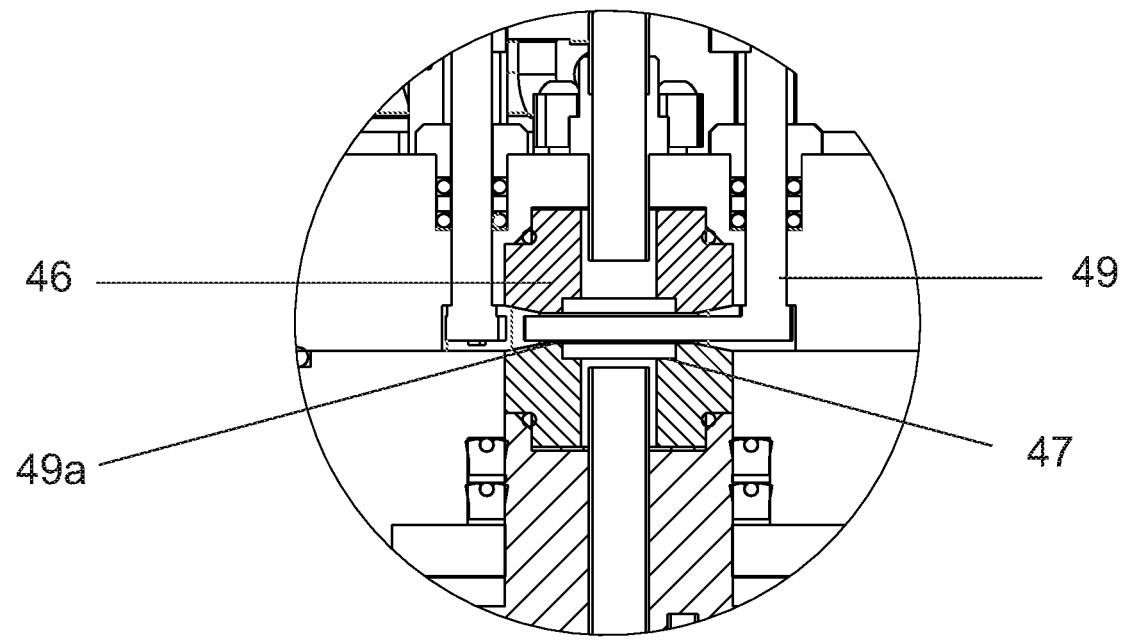
Figure 7A:
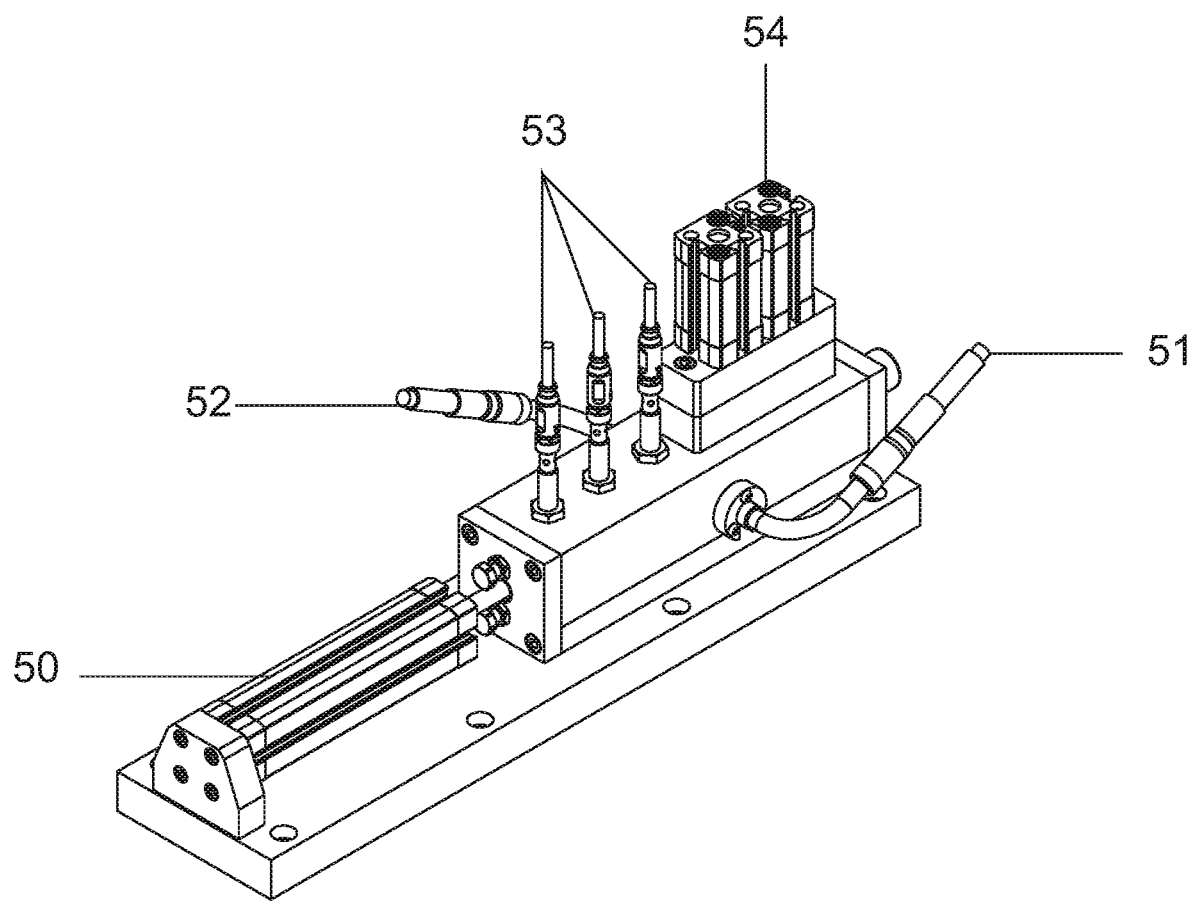
FIG. 7A presents a perspective view of the optical calibration module ($M_{cal}$)
Figure 7B:
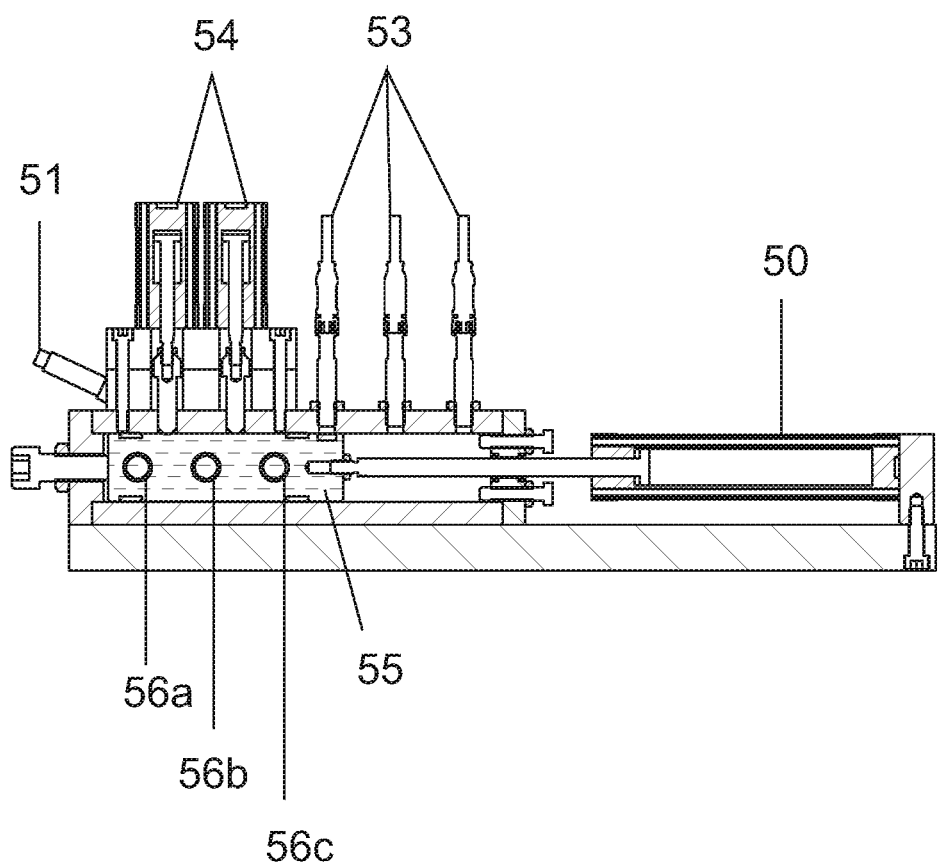
FIG. 7B presents a longitudinal sectional view and FIG. 7C presents the sectional detail of the internal elements.
Figure 7C:
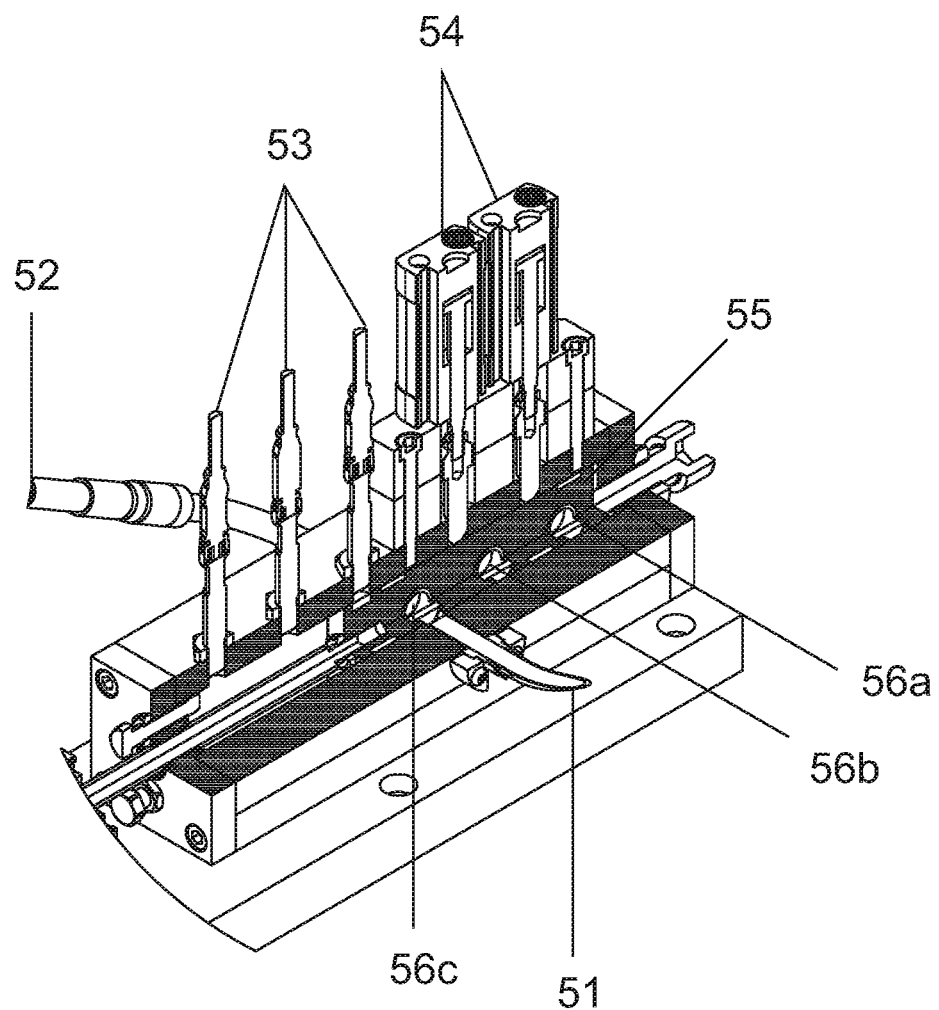

After the conclusion of the transference of the "analytical package" to the interior of the analytical chamber (49a) of the fluid analysis module ($M_{anflu}$), by the total contraction of the volume of the mixing chamber (39), as detailed in FIG. 5E, the control unit ($U_{cont}$) commands the actuation of the pneumatic actuator (45) to the positioning of the reading optical windows (46) and (46) to the fixed measurement thickness, according to FIG. 6E.

After the confirmation of the positioning by the control unit ($U_{cont}$), by means of the position sensors of this pneumatic actuator (45), the analytical procedure begins.

During the analytical characterization, the sample of the fluid material contained between the optical windows (46) and (47) is irradiated by means of the electromagnetic radiation produced by the luminous source ($F_{lum}$) in the region from 100 to 6000 nanometers, being conducted by the optical fibers beam (44).

The electromagnetic radiation conducted by the optical fibers beam (44) then crosses the movable optical window (47), interacting with the sample of fluid for analysis contained between the optical windows (46) and (47) and emerging on the opposite side of the irradiation.

The product of the interaction between the electromagnetic radiation and the sample then crosses the optical window (46) and is collected by the capture optical fibers beam (43), being in this manner conducted to the double beam spectrophotometer (Esp).

The double beam spectrophotometer (Esp) in this type of application can be qualified for analysis from the ultraviolet range up to the infrared range (100 to 6000 nanometers), providing great analytical versatility for the equipment and analytical method described herein, generating information associated to the referred physical characteristic of the fluid which is forwarded to the control unit where the microprocessor processes the spectrophotometric measurements by transmission analysis which by means of the mathematical processing, presents the results of the analysis in the microcomputer.

During the next sequencing step, the control unit ($U_{cont}$), must carry out the decontamination of the optical windows (46) and (47), before the next reading cycle, and for this purpose the control unit ($U_{cont}$), will initially command the retreat of the positioning pneumatic actuator of the optical windows (45).

Once the position of retreat and the distancing of the optical windows is confirmed, by means of the position sensors of the pneumatic actuator (45), the mechanical cleaning arms (49), connected to the pneumatic actuators (40), will be activated by the control unit ($U_{cont}$).

The mechanical cleaning arms (49) are redundant, and the pneumatic actuators thereof (40) provide a rotary scraping of the pallets (49b) manufactured from a special elastomer, which are conducted by means of the cleaning arms (49) over the surface of the optical windows (46) and (47).

The pneumatic actuators (40), activated by the cleaning arms (49) have an electronic interlocking cycle commanded by the control unit ($U_{cont}$).

After this final step, the analytical cycle already previously described is reinitiated.

For the calibration of the spectrophotometer, there is foreseen an optical calibration module ($M_{cal}$), commanded by the control unit ($U_{cont}$), which introduces in the sample channel of the spectrophotometer (Esp), a set of neutral optical filters (56a), (56b) and (56c), having known attenuation, fixed to a positioning block (55), which block part of the luminous radiation that reaches the detector of the spectrophotometer, avoiding the "saturation" thereof during the calibration phase.

The movement of the "neutral optical filters" (56a), (56b) and (56c), is carried out by means of the pneumatic actuator positioner (50), there being possible the positioning of three cited neutral filters, there further existing two other auxiliary pneumatic actuators (54), which introduce mechanical stops in the positioning points of the "neutral optical filters" (56a), (56b) and (56c).

The position sensors (53) provide information as to the confirmation of the position of the "neutral optical filters" (56a), (56b) and (56c), to the control unit ($U_{cont}$).

For the cleaning of the equipment and in order to clean the surfaces for analysis of a distinct product, the control unit ($U_{cont}$) switches the second selector valve ($V_{sel2}$) to the third position, allowing the admission of the cleaning solvent stored in container C3 at the admission point (18c) of the first selector valve ($V_{sel1}$), and the second selector valve ($V_{sel2}$) can also be activated for the passage of the solvent through all the equipment.

The invention claimed is:
1. A system for fluid analysis comprising:
a control unit;
a property measurement cell;
a luminous source;
a container (C1) configured to contain a first constituent part of the fluid;
a container (C2) configured to contain a second constituent part of the fluid;
a container (C3) configured to contain a third constituent part of the fluid;
a first selector valve in fluid communication with the containers;
a dosing module in fluid communication with the first selector valve;
a second selector valve in fluid communication with the dosing module;
a mixing module in fluid communication with the second selector valve; and
a spectrophotometer;
wherein a value of a property of a fluid sample is analyzed in the property measurement cell;
wherein the property measurement cell comprises an analytical chamber having a static optical window and a movable optical window between which windows a thickness of the fluid sample is defined by the control unit;
wherein the luminous source is configured to provide electromagnetic radiation to interact with the fluid sample for analysis by the spectrophotometer;
wherein the first selector valve has a first rotating flange moved by a first rotary actuator, the first rotary flange presenting a set of first stop positions, the set of first stop positions having positioning controlled by the control unit and by first selector valve stops commanded by a first stop actuator, the first selector valve configured to receive at least a portion of the first, second and third constituent parts of the fluid;
wherein the dosing module is configured to dose a volume of fluid for analysis and is controlled by the control unit;

wherein the second selector valve has a second rotating flange moved by a second rotary actuator, the second rotary flange presenting a set of second stop positions, the set of second stop positions having positioning controlled by the control unit and by second selector valve stops commanded by a second stop actuator;

wherein the mixing module comprises a mixing chamber in which the dosed volume of fluid is mixed upstream the property measurement cell; and wherein the first selector valve presents:
a first stop position of the first set of stop positions that allows the admission of the first constituent part of the fluid from the container (C1) to an entry point of the first selector valve;
a second stop position of the first set of stop positions that allows the admission of the second constituent part of the fluid from the container (C2) to the entry point of the first selector valve;
a third stop position of the first set of stop positions that allows the admission of the third constituent part of the fluid from the container (C3) to the entry point of the first selector valve; and
a fourth stop position of the first set of stop positions that blocks the passage of fluid in all directions.

2. The system according to claim 1 further comprising a first combiner configured to combine the first constituent part of the fluid with the second constituent part of the fluid in a first ratio forming a first sample of the fluid, the first combiner controlled at least in part by the control unit;
wherein the first sample is the fluid sample analyzed in the property measurement cell;
wherein the first constituent part of the fluid is drawn into the first combiner via suction from a first pump located downstream the container (C1) and upstream the first combiner; and
wherein the second constituent part of the fluid is drawn into the first combiner via suction from a second pump located downstream the container (C2) and upstream the first combiner.

3. The system according to claim 1, wherein the spectrophotometer comprises a double beam spectrophotometer configured to provide electromagnetic radiation in a range from the ultraviolet to the infrared.

4. The system according to claim 1, wherein the property measurement cell further comprises mechanical cleaning arms coupled to pneumatic actuators activated by the control unit, the mechanical cleaning arms provided with elastomeric pallets for scraping one or more surfaces of one or both of the static optical window and the movable optical window.

5. The system according to claim 1 further comprising an optical calibration module commanded by the control unit, which introduces a set of neutral optical filters to the spectrophotometer, the neutral optical filters having known attenuation and fixed to a positioning block with position sensors and moved by pneumatic actuators that introduce mechanical stops at positioning points of the neutral optical filters.

6. A system for fluid analysis comprising:
a control unit;
a property measurement cell;
a luminous source;
a spectrophotometer;
a first selector valve having a first rotating flange moved by a first rotary actuator;
a dosing module in fluid communication with the first selector valve;
a second selector valve in fluid communication with the dosing module;
a mixing module in fluid communication with the second selector valve; and
a fluid analysis module in fluid communication with the mixing module;
wherein:
a value of a property of a fluid sample is analyzed in the property measurement cell;
the property measurement cell comprises an analytical chamber having a static optical window and a movable optical window between which windows a thickness of the fluid sample is defined by the control unit;
the luminous source is configured to provide electromagnetic radiation to interact with the fluid sample for analysis by the spectrophotometer;
the first rotary flange presents a set of first stop positions, the set of first stop positions having positioning controlled by the control unit and by first selector valve stops commanded by a first stop actuator;
the dosing module is configured to dose a volume of fluid for analysis and is controlled by the control unit;
the second selector valve has a second rotating flange moved by a second rotary actuator, the second rotary flange presenting a set of second stop positions, the set of second stop positions having positioning controlled by the control unit and by second selector valve stops commanded by a second stop actuator;
the mixing module comprises a mixing chamber in which the dosed volume of fluid is mixed upstream the property measurement cell; and
the fluid analysis module comprises:
the property measurement cell;
the luminous source; and
the spectrophotometer comprising a double beam spectrophotometer.

7. The system according to claim 6, wherein the analyzed property of the fluid sample is selected from the group consisting of color, opacity, hue, saturation, tinting power, covering and luminosity.

8. The system according to claim 6 further comprising two or more containers, each configured to contain a constituent part of the fluid, the containers located upstream the first selector valve;
wherein the first selector valve is configured to provide the dosing module with a first ratio of the constituent parts of the fluid;
wherein the value of the property of the fluid sample comprising the first ratio of the constituent parts is compared to a desired value of the property of the fluid sample; and
wherein the control untl controls the first selector valve to provide the dosing module with a second ratio of the constituent parts of the fluid such that the value of the property of the fluid sample comprising the second ratio of the constituent parts is closer to the desired value of the property of the fluid sample than the value of the property of the fluid sample comprising the first ratio of the constituent parts.

9. The system according to claim 8, wherein each constituent part of the fluid is drawn into the first selector valve by two or more pumps, one each located downstream each container and upstream the first selector valve.

10. The system according to claim 8, wherein the two or more containers comprise:
a container (C1) containing a first constituent part of the fluid;
a container (C2) containing a second constituent part of the fluid; and
a container (C3) containing a third constituent part of the fluid;
wherein the first selector valve presents a first stop position of the first set of stop positions that allows the admission of the first constituent part of the fluid from the container (C1) to an entry point of the first selector valve;
wherein the first selector valve presents a second stop position of the first set of stop positions that allows the admission of the second constituent part of the fluid from the container (C2) to the entry point of the first selector valve;
wherein the first selector valve presents a third stop position of the first set of stop positions that allows the admission of the third constituent part of the fluid from the container (C3) to the entry point of the first selector valve; and
wherein the first selector valve presents a fourth stop position of the first set of stop positions that blocks the passage of fluid in all directions.

11. The system according to claim 8, wherein the dosing module comprises a dosing syringe and plunger, the plunger controlled by a linear positioner actuated by a motor; and
wherein the plunger is configured to retreat until a volume of fluid for analysis is reached.

12. The system according to claim 8, wherein the mixing module comprises:
a mixing chamber;
a helical conical agitator;
a motor;
a movable wall; and
a mover;
wherein the helical conical agitator is located within the mixing chamber and connected to an axis driven by the motor; and
wherein the movable wall defines one end of the mixing chamber and is driven by the mover.

13. The system according to claim 6 further comprising:
a container (C1) containing a first constituent part of the fluid;
a container (C2) containing a second constituent part of the fluid; and
a container (C3) containing a third constituent part of the fluid;
wherein each of the containers is located upstream the first selector valve;
wherein the dosing module comprises a dosing syringe and plunger, the plunger controlled by a linear positioner actuated by a motor;
wherein the plunger of the dosing module is configured to retreat until a volume of fluid for analysis is reached;
wherein the first selector valve is configured to provide the dosing module with a first ratio of the constituent parts of the fluid;
wherein the property of the fluid sample comprising the first ratio of the constituent parts is compared to a desired property of the fluid sample;
wherein the control until controls the first selector valve to provide the dosing module with a second ratio of the constituent parts of the fluid such that the property of the fluid sample comprising the second ratio of the constituent parts is closer to the desired property of the fluid sample than the property of the fluid sample comprising the first ratio of the constituent parts;
wherein the analyzed property of the fluid sample is selected from the group consisting of color, opacity, hue, saturation, tinting power, covering and luminosity;
wherein the first selector valve presents a first stop position of the first set of stop positions that allows the admission of the first constituent part of the fluid from the container (C1) to an entry point of the first selector valve;
wherein the first selector valve presents a second stop position of the first set of stop positions that allows the admission of the second constituent part of the fluid from the container (C2) to the entry point of the first selector valve;
wherein the first selector valve presents a third stop position of the first set of stop positions that allows the admission of the third constituent part of the fluid from the container (C3) to the entry point of the first selector valve; and
wherein the first selector valve presents a fourth stop position of the first set of stop positions that blocks the passage of fluid in all directions.

14. The system according to claim 13, wherein the mixing module comprises:
a mixing chamber;
a helical conical agitator;
a motor;
a movable wall; and
a mover;
wherein the helical conical agitator is located within the mixing chamber and connected to an axis driven by the motor; and
wherein the movable wall defines one end of the mixing chamber and is driven by the mover.

15. A method comprising:
analyzing with a system for fluid analysis a value of a property of a fluid sample comprising a first ratio of constituent parts, wherein the analyzing comprises:
defining a thickness of a testing portion of the fluid sample between a static optical window and a movable optical window;
irradiating through the windows the testing portion of the fluid sample by a luminous source; and
detecting the interaction of the fluid sample with the radiation by a spectrophotometer;
comparing the analyzed value against a desired value; and
preparing a second fluid sample comprising a second ratio of the constituent parts different from the first ratio;
wherein the value of the property of the second fluid sample comprising the second ratio of the constituent parts is closer to the desired value than the analyzed value of the property of the first fluid sample comprising the first ratio of the constituent parts;
wherein the system for fluid analysis comprises a fluid analysis module including the windows, the luminous source, and the spectrophotometer;
wherein the system for fluid analysis further comprises:
a control unit;
a first selector valve having a first rotating flange moved by a first rotary actuator;
a dosing module in fluid communication with the first selector valve;
a second selector valve in fluid communication with the dosing module; and a mixing module in fluid communication with the
second selector valve;
wherein the fluid analysis module is in fluid communication with the mixing module;
wherein the first rotary flange presents a set of first stop positions, the set of first stop positions having positioning controlled by the control unit and by first selector valve stops commanded by a first stop actuator;
wherein the dosing module is configured to dose a volume of the fluid sample for analysis and is controlled by the control unit;
wherein the second selector valve has a second rotating flange moved by a second rotary actuator, the second rotary flange presenting a set of second stop positions, the set of second stop positions having positioning controlled by the control unit and by second selector valve stops commanded by a second stop actuator; and
wherein the mixing module comprises a mixing chamber in which the dosed volume of fluid is mixed upstream the windows.

* * * * *